(12) United States Patent
Mandaroux

(10) Patent No.: US 10,751,484 B2
(45) Date of Patent: Aug. 25, 2020

(54) NEEDLE ARRAY DEVICE

(71) Applicant: Allergan Industrie SAS, Pringy (FR)

(72) Inventor: Bastien Mandaroux, Metz-Tessy (FR)

(73) Assignee: Allergan Industrie, SAS, Pringy (FR)

( * ) Notice: Subject to any disclaimer, the term of this patent is extended or adjusted under 35 U.S.C. 154(b) by 160 days.

(21) Appl. No.: 15/934,904

(22) Filed: Mar. 23, 2018

(65) Prior Publication Data

US 2018/0264204 A1   Sep. 20, 2018

Related U.S. Application Data

(60) Provisional application No. 62/450,921, filed on Jan. 26, 2017.

(51) Int. Cl.
| | |
|---|---|
| A61M 5/32 | (2006.01) |
| A61M 5/315 | (2006.01) |
| A61M 5/42 | (2006.01) |
| A61M 5/46 | (2006.01) |
| A61M 39/10 | (2006.01) |

(52) U.S. Cl.
CPC ...... *A61M 5/3295* (2013.01); *A61M 5/31545* (2013.01); *A61M 5/3293* (2013.01); *A61M 5/42* (2013.01); *A61M 5/46* (2013.01); *A61M 39/105* (2013.01); *A61M 5/3202* (2013.01); *A61M 2005/31588* (2013.01); *A61M 2205/3327* (2013.01); *A61M 2205/3344* (2013.01); *A61M 2210/0606* (2013.01)

(58) Field of Classification Search
CPC .............. A61M 5/3295; A61M 5/3293; A61M 5/3297; A61M 5/3298; A61M 5/46; A61M 39/105; A61M 2005/342; A61M 2037/003
See application file for complete search history.

(56) References Cited

U.S. PATENT DOCUMENTS

| | | | | |
|---|---|---|---|---|
| 3,595,231 A | * | 7/1971 | Pistor | A61M 5/3298 604/173 |
| 2013/0102954 A1 | * | 4/2013 | Choi | A61N 1/327 604/21 |

FOREIGN PATENT DOCUMENTS

EP       3085410 A1 * 10/2016 ............. A61M 5/20

* cited by examiner

*Primary Examiner* — Kami A Bosworth
*Assistant Examiner* — Antarius S Daniel
(74) *Attorney, Agent, or Firm* — Nathan S. Smith; Danny Mansour; Morgan, Lewis & Bockius LLP

(57) ABSTRACT

A needle injection array can comprise a plurality of needles that are fluidly interconnected via a fluid manifold. The fluid manifold can be configured to direct fluid from a syringe to arrive at tips of the needles approximately simultaneously. The fluid manifold also be configured to provide approximately equal dosage or fluid volume through each of the needles to an injection site.

20 Claims, 10 Drawing Sheets

NEEDLE ARRAY DEVICE

CROSS-REFERENCE TO RELATED APPLICATIONS

This application claims the benefit of and priority to related U.S. Patent Provisional Application No. 62/450,921, filed on Jan. 26, 2017, the entirety of which is incorporated herein by reference.

BACKGROUND

Field of the Inventions

The present disclosure generally relates to mechanisms for injection and dosing, and more specifically, to devices for providing even and/or simultaneous dosage of a fluid, such as a dermal filler, to a target site.

Description of the Related Art

Aesthetic dermal filler procedures have become increasing popular in recent years, as they have proven to be quite effective in improving the appearance of the face, for example, in reducing the signs of aging by smoothing wrinkles and folds, such as the nasolabial folds, and plumping the midface. Some of the more popular dermal fillers are soft, colorless gel compositions made of hyaluronic acid. Hyaluronic acid (HA) is a long chain polymer, more specifically, a polysaccharide, which occurs naturally in body tissues. When chemically crosslinked, hyaluronic acid makes an excellent, long lasting, dermal filler material. Dermal filler procedures are quite minimally invasive, and the results are nearly immediate. Further, hyaluronic acid naturally degrades in the body tissues, and thus the fillers are temporary, for example, lasting several months to a year or more. Further, results of hyaluronic acid based dermal filler procedures can be reversed using hyaluronidase.

Conventional dermal filler procedures are generally performed by injection of the composition into or below the skin using a standard syringe and a fine gauge needle. A typical dermal filler patient may undergo from about 5 to about 10 injections in a single procedure, with injection points across various regions of the face, neck, décolletage, hands, or other such areas. While the goal may be to improve the appearance of the entire face, a skilled aesthetic physician generally aims to correct one or more specific regions of the face, for example, regions that lack volume such as the lips or the cheeks, or regions that present specific wrinkles, such as deep nasolabial folds, with specific input from the patient regarding areas he or she finds detracting to his or her appearance. Injections are typically for volumetric improvement, sculpting, and/or wrinkle filling. These corrective areas typically represent specific regions (i.e., lips, brow, radial cheek lines, etc.).

SUMMARY

As noted, HA gel can be used as well to improve overall skin quality of a large surface area, such as the entire face, neck décolletage, hands or other such areas via typical needle injection. To improve skin quality of these surface areas, anywhere from tens to thousands of injections must be made. However, in accordance with at least some embodiments disclosed herein is the realization that it would not be practical or efficient to perform hundreds or thousands of injections to treat a given area.

Moreover, when tested with HA gel as the delivery fluid, existing conventional needle array devices were not able to: (1) handle the pressure required to inject the HA-gel-based implant and did show leakage; (2) allow acceptable dosage discrepancy across needles; (3) allow acceptable dosage discrepancy per needle across multiple injection cycle; (4) perform aspiration to test if at least one of the needle is located within a blood vessel; and/or (5) keep at minimum the amount of HA gel that fills, but is not expelled from (and thus lost) within the multi-needle.

Accordingly, in some embodiments, a needle array device is provided that can allow for controlled depth of injection. This feature is adjustable during the manufacturing process (sleeves with different length being assembled) but non-adjustable by the end user (e.g., the end user may have the choice within a range of SKU having different length only). However the depth at which it can deliver gel can be between 500 microns and 5000 microns.

Further, the device can allow for even flow of product across the needles attached to the Juvederm needle array. The device can be capable of providing anywhere from 5 µL to 500 µL doses at each injection site.

The device can allow aspiration when located at the injection site, thus making it possible for the end user to check if one or more needles are within a blood vessel.

The device or procedure can be faster than otherwise possible compared to procedures using a standard needle and syringe. Additionally, the device can work with existing gel packaging techniques (standard sized syringes, e.g., 1 mL COC syringe).

In some embodiments, the present disclosure relates to a medical device used to provide an injection of a HA-gel-based implant in a patient's body simultaneously through multiple mini-invasive surgical procedures.

In some embodiments, the device can comprise a support base having one or more flow channels that facilitate the delivery of fluid to each of the needle tips of the device approximately simultaneously. Further, in some embodiments where the needles have different lengths, the configuration of the flow channels to be configured differently from each other to ensure that fluid reaches outlet ends of the flow channels at different moments to tend to ensure that the fluid reaches the tips of the needles approximately simultaneously.

In some embodiments, the medical device can comprise a needle hub connector or support or needle base to distribute the product flow to the multiple needles in an array. The array can comprise at least 2 needles (e.g. hypodermic needles) connected to the needle base. Further, the device can comprise a sleeve to define an exposed needle length.

The needle base can be used to split the flow of product coming from the syringe by the needle hub into various channels pathways to permit fluid flow to reach the tips of each of the individual needles attached to this needle base. These path ways being design to ensure that the injected HA-gel-based implant will reach the tips and/or needle aperture to simultaneously enter or exit each needle. Each needle can be designed to ensure that the injected HA-gel-based implant reaches the tip of these needles approximately simultaneously.

The sleeve can be used to leave exposed the desired exposed needle length. During the injection the sleeve can prevent further insertion of the needle under the skin, insuring that when the user applies the right pressure each needle is injecting within the same depth. The sleeve can be adjustable or interchangeable during the manufacturing process (e.g., sleeves with different length being assembled into the needle base) but non-adjustable by the end user (e.g., the end user may have the choice within a range of SKU having different lengths only).

An advantage of some embodiments disclosed herein is the ease of use it to inject an HA-gel-based implant at a desired depth and appropriate injection site distance to each other. The end user just needs to ensure that the sleeve is in contact with the patient skin across each needle. At each injection at least two injection sites are being treated.

Another advantage of some embodiments disclosed herein is the fact that aspiration could be performed to ensure that the needle is not within the blood vessel. The needle array is designed to ensure flow of gel and liquid in both directions and with no air leakage through the gel/liquid channels.

Yet another advantage of some embodiments disclosed herein is the low dosage discrepancy across needles and low dosage discrepancy per needle across multiple injection cycle, which can be due to the flow channel design to ensure that the product will reach simultaneously each needle. But also due to the geometry and air tightness of the channels to ensure that no air bubbles could remain trapped within the needle array.

In accordance with some embodiments disclosed herein, the flow channels of the support bases can have a round, circular, polygonal, or square cross-sectional shape.

The following embodiments represent mechanisms that may be used to achieve one or more of the above value propositions. Note that in order to create a complete device capable of meeting all of the above, one or more of these embodiments may need to be combined with one another.

Additional features and advantages of the subject technology will be set forth in the description below, and in part will be apparent from the description, or may be learned by practice of the subject technology. The advantages of the subject technology will be realized and attained by the structure particularly pointed out in the written description and embodiments hereof as well as the appended drawings.

It is to be understood that both the foregoing general description and the following detailed description are exemplary and explanatory and are intended to provide further explanation of the subject technology.

BRIEF DESCRIPTION OF THE DRAWINGS

Various features of illustrative embodiments of the inventions are described below with reference to the drawings. The illustrated embodiments are intended to illustrate, but not to limit, the inventions. The drawings contain the following figures.

DETAILED DESCRIPTION

Figure 1:
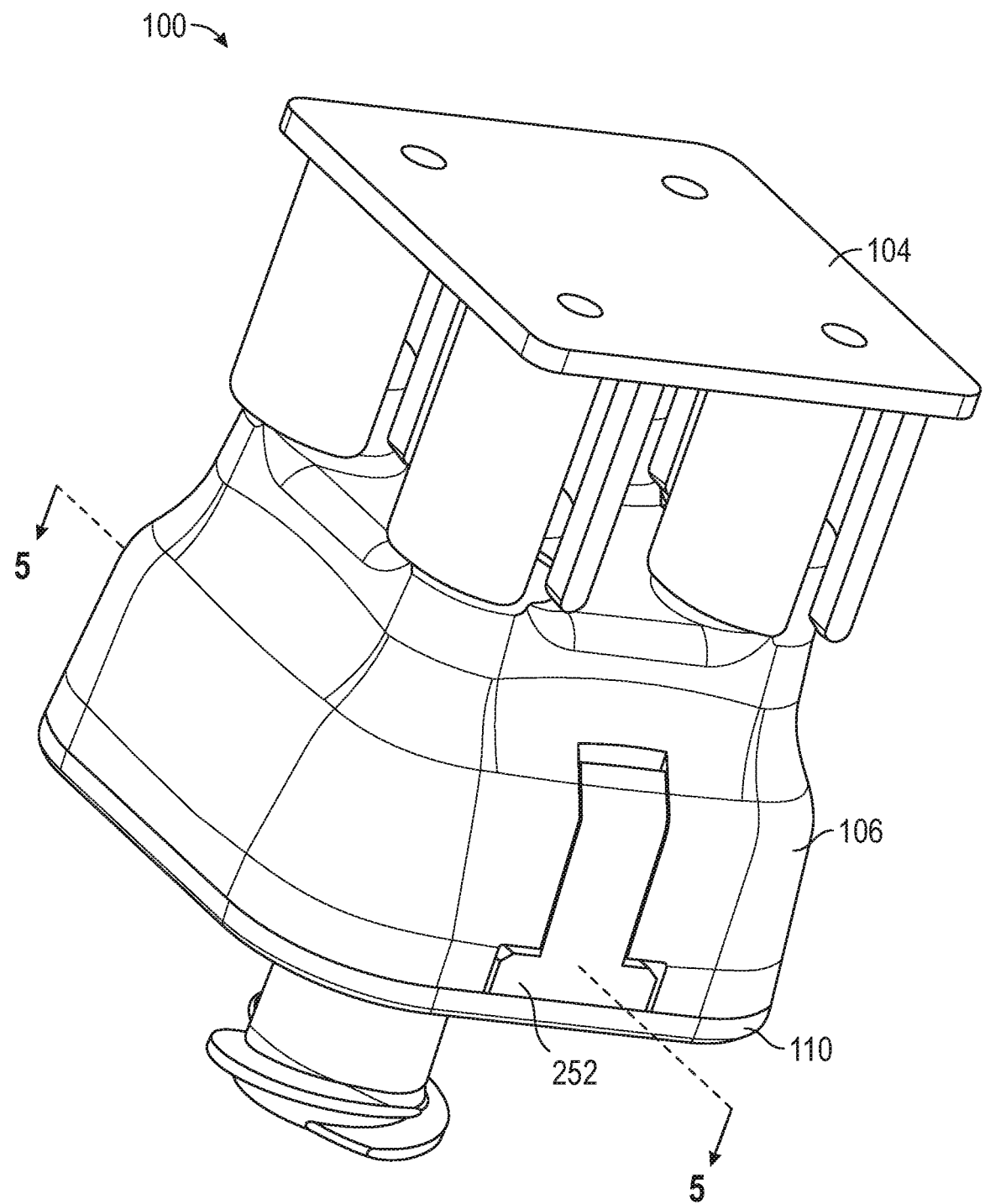
FIG. 1 is a front perspective view of a 2×2 needle array device, according to some embodiments.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology. Like components are labeled with identical element numbers for ease of understanding.

The present application addresses several operational challenges encountered with needle array devices and related procedures. This application provides numerous improvements that enable ejection of a medicament from a plurality of needles in an even and balanced manner. For example, in accordance with some embodiments, the present application discloses a needle array device that can be used to eject a medicament from each of a plurality of needles at approximately the same time, pressure, and/or volume.

Further, some embodiments of the needle array device and related procedures disclosed herein can advantageously control a depth of insertion of a plurality of needles in a needle array device, aspiration of an injection site of a plurality of needles in a needle array device, and restrict air from being retained in a medicament pathway of a needle array device.

Referring to the figures, a needle array device 100 is illustrated in FIGS. 1-3B. A needle array device 100 can comprise needles 102, a removable protector 104, a sleeve 106, a needle assembly 108, and a support base 110. Features of some embodiments can be used in a handheld device or incorporate other aspects of copending U.S. Patent Application Publication US2016/0095984A1, the entirety of which is incorporated herein by reference for all purposes.

The needle array device 100 can comprise a plurality of needles 102. The needles 102 are configured to be inserted into a patient and to direct a medicament into the patient in situ. Although this application describes the medicament as a gel, the medicament can be substance configured to be ejected by a needle, including, liquids and gasses. In some examples, the medicament is an injectable hyaluronic acid gel.

Figure 2:
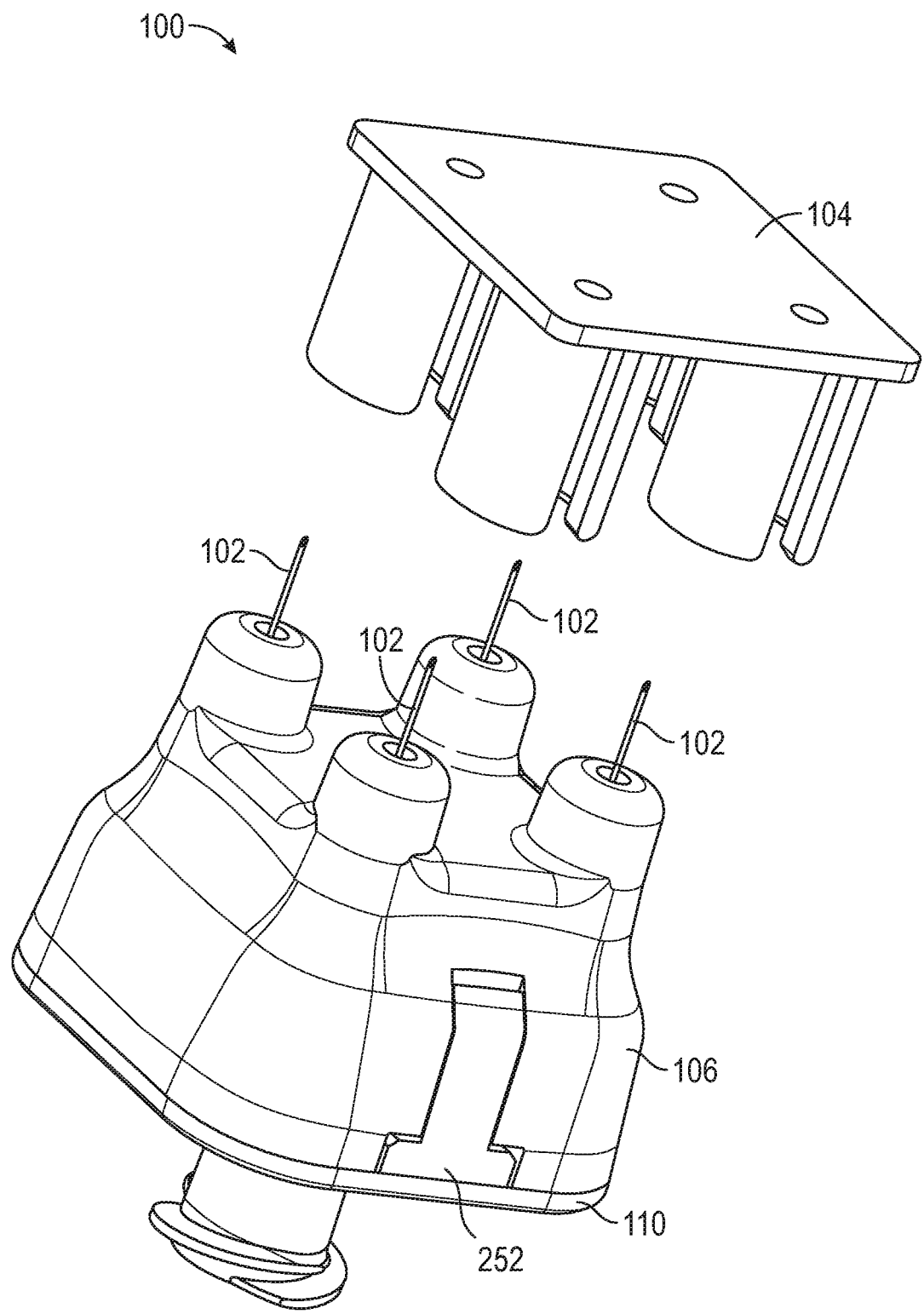
FIG. 2 is a partially exploded view of a needle array device, according to some embodiments.
Figure 3A:
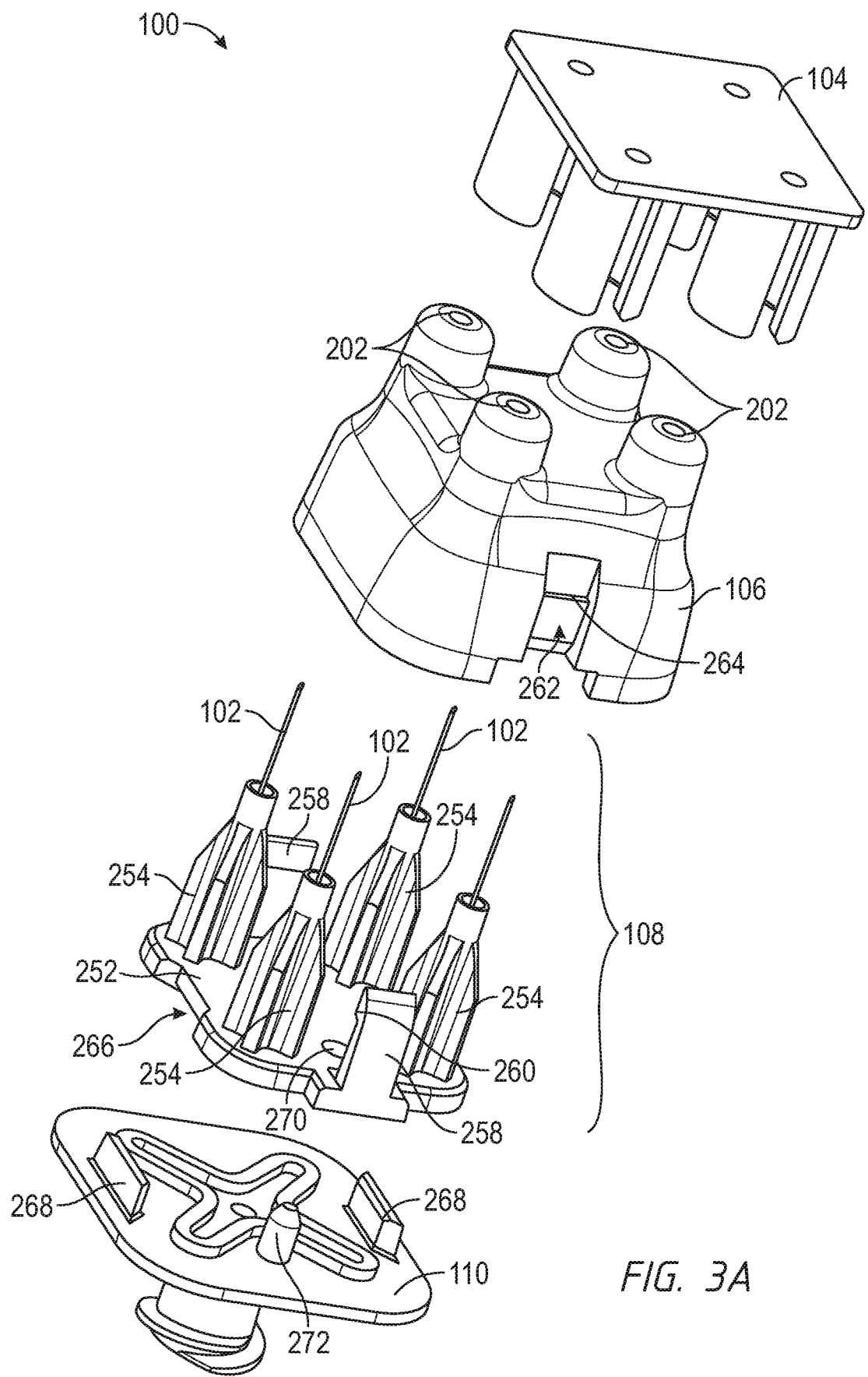
FIGS. 3A and 3B are exploded views of a needle array device, according to some embodiments.
Figure 3B:
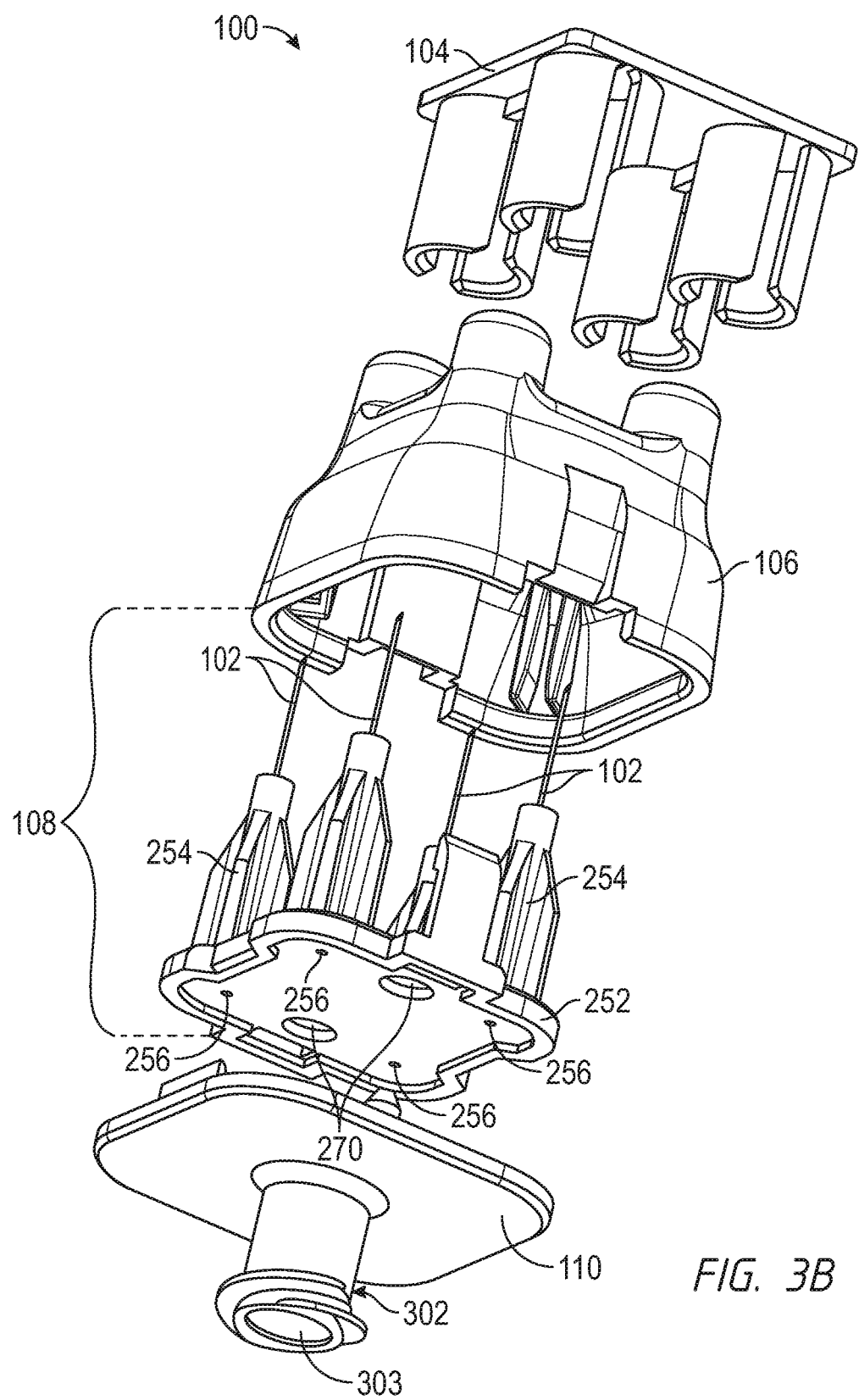

The plurality of needles 102 of the needle array device 100 can include two or more needles 102 arranged in a pattern. The needles 102 can be arranged in a symmetrical pattern, for example a square, circle, or straight line, or a non-symmetrical pattern. Referring to FIGS. 2-3B, four needles 102 are arranged approximately as a square forming a 2×2 pattern.

The needles 102 can include a base portion and a tip portion. The base portion can be coupled to a portion of the needle array device 100 so that the tip portion extends away from the needle array device 100. A passage extends through each needle 102, from the base portion through the tip portion. The passage directs a medicament through the needle for ejection at the tip portion. In some examples, the tip portion comprises a beveled surface with the passage extending through the bevel. The beveled surface of the tip portion can facilitate piercing the skin or other surface of a patient.

The needles 102 can be at least about 34 gauge and/or less than or equal to about 20 gauge. In some examples, the needle size is between at least about 34 gauge and/or less than or equal to about 23 gauge.

The needle array device 100 can include a removable protector 104 configured to prevent unintentional contact with the needles 102. The removal protector 104 can comprise a cover plate 152 and walls 154 that extends over an outer surface of the needles 102.

The size and shape of the removal protector 104 corresponds to the arrangement of the needles 102. The cover plate 152 comprises a size sufficient to extend across the tip portions of each of the needles 102. The walls 154 are positioned to correspond with the arrangement of the needles 102 so that the walls 154 extend over a needle 102 when the removable protector 104 is coupled with the needle array device 100.

The walls 154 can extend from the cover plate 152 and comprise a cylindrical cross-section having one or more notches. Referring to FIGS. 1-3B, cylindrically shaped walls 154 are positioned in a 2×2 pattern with a longitudinal axis of each cylindrical wall aligned with a longitudinal axis of each needle 102. Further, in some embodiments, openings through the removable protector 104 are aligned with the longitudinal axis of each needle 102.

A cross-sectional inner profile of the cylindrical walls 154 is configured to receive a portion of the needle array device 100. In some embodiments, the cross-sectional inner profile of the cylindrical walls 154 is approximately equal to or less than an outer surface of the needle array device 100.

When the removable protector 104 is coupled with the needle array device 100, the notches permit portions of the wall 154 to be urged to provide an interference fit between the removable protector 104 and the needle array device 100. Although interference fit between the removable protector 104 and the needle array device 100 is described, other means of coupling can be implemented. For example, the removal protector 104 can be coupled with the needle array device 100 using a mechanical connection or adhesive. In some embodiments, the removal protector 104 and the needle array device 100 can be unitarily formed with a break-away portion or living hinge.

The needle array device 100 can include a sleeve 106 configured to limit the depth that the needles 102 can be inserted into a patient. Depending on the type of procedure or treatment, a user can select a sleeve 106 for coupling with the needle array device 100 to achieve a desired injection depth. The depth that the needles 102 can be inserted into a patient is limited by the length of the portion of each needle 102 that extends beyond an outer surface of the sleeve 106. When the plurality of needles 102 are advanced into the patient, contact of the outer surface of the sleeve 106 against the patient and prevents further insertion of the needles 102.

The size and shape of the sleeve 106 can be based on the number and arrangement of the plurality of needles 102. Referring to FIGS. 1-3B, the sleeve 106 comprises a proximal portion and a distal portion. An inner cavity extends from the proximal portion toward a distal portion. The inner cavity is configured to receive a portion of the needles 102 and can comprise a cross-sectional profile that is approximately equal to or greater than a perimeter around the plurality or needles 102.

The distal portion of the sleeve 106 comprises a plurality of heads, each head having an opening 202 to permit a portion of the needles 102 to extend therethrough. The openings 202 are positioned in a pattern that corresponds with the arrangement of the plurality of needles 102. For example, the openings 202 of the sleeve illustrated in FIGS. 1-3B are positioned in a 2×2 square pattern.

The length of the portion of each needle 102 that is exposed or extends beyond an outer surface of the head of the sleeve 106 depends on the length (or height) of the sleeve 106, which can be measured from the proximal portion to an outer surface of the sleeve at the distal portion. If the head or sleeve length (or height) increases, the exposed length of the needle 102 decreases, and conversely, the head or sleeve length decreases, the exposed length of the needle 102 increases. Accordingly, in some embodiments, needle array kits can be provided in which a variety of sleeves having different head or sleeve lengths can be configured to couple with the needle array device 100. A sleeve 106 having a particular length can be selected to limit the depth that the needles 102 can be inserted into a patient. For example, when a sleeve 106 having a short length, relative to the length of the needles 102, is coupled with the needle array device 100, the portion of each needle 102 that extends beyond an outer surface of the sleeve 106 is greatest. Therefore the depth that the needles 102 can be inserted into a patient is greatest. To the contrary, when a sleeve 106 having a long length, relative to the length of the needles 102, is coupled with the needle array device 100, the portion of each needle 102 that extends beyond an outer surface of the sleeve 106 is minimal. Therefore the depth that the needles 102 can be inserted into a patient is minimal.

In some examples, the sleeve 106 can comprise individual wall portions that extend around each needle 102. An outer surface of the sleeve 106 can comprise a plurality of concave portions. The number and position of each concave portion corresponds with the number and arrangement of the plurality of needles 102, such that a needle 102 extends through each of concave portion.

Depending on the sleeve 106 coupled to the needle array device 100, the needles 102 can extend beyond an outer surface of the sleeve 106 to provide an exposed height. The exposed height of a needle 102 corresponds to a depth that the needle 102 can be inserted into a patient. A needle 102 can have an insertion depth of at least about 0.5 mm and/or less than or equal to about 5 mm. In some examples, the needles 102 can extend beyond an outer surface of the sleeve 106 by at least about 1.5 mm and/or less than or equal to about 3.5 mm. In some embodiments, the needles 102 have an exposed height between about 1 mm and about 5 mm, between about 2 mm and about 4 mm, or about 3 mm.

After the needles 102 have been inserted into a patient, a user may optionally perform an aspiration gesture to ensure that the needles 102 are not within a blood vessel. If no blood is seen within a Luer connector of the needle array device 100 and/or syringe coupled to the needle array device 100, the user can proceed to injection the medicament.

The needle array device 100 can include a needle assembly 108 comprising a needle base 252, and two or more needle columns 254 and needles 102.

The needle base 252 can comprise an upper portion and a lower portion. The upper portion can comprise a top surface, and the lower portion can comprise a bottom surface. The needle columns 254 extend from the top surface of the needle base 252 and are configured to support the needles 102. Each needle column 254 can comprises a protrusion or shaft that extends from the needle base 252 with a needle 102 extending from each needle column 254. One or more wings extend radially outward from the shaft of the needle column 254 to provide support or buttressing. In some embodiments, the needle column 254 can comprises a cone shape having a cross-sectional profile that tapers away from the needle base 252.

The needle columns 254 are positioned, relative to each other, to form the arrangement of the plurality of needles 102. For example, four needle columns 254 can extend from the needle base 252 in a generally square pattern to form the 2×2 arrangement illustrated in FIGS. 3A and 3B. The number of needle columns 254 and their position on the needle base 252 is not limited to a 2×2 arrangement. In should be understood that embodiments of the present application can comprise needle columns 254 and needles 102 positioned to form a variety of arrangements that can include, but are not limited to, a 1×4, a 1×6, or a 2×4 array. Further, the needle columns 254 and needles 102 can be positioned to form a variety arrays, including circles, triangles, parabolas, and irregular or non-symmetrical arrays. Depending on the type of procedure or treatment, a user can select a needle array device having desired needle arrangement pattern, spacing between needles, and possible needle insertion depth.

The needles 102 are be positioned an equal distance apart from each other. The needles 102 can be positioned, relative to each other, with a distance of at least about 3 mm and/or less than or equal to about 32 mm. In some examples, a distance between each of the needles 102 is at least about 5 mm and/or less than or equal to about 30 mm.

Although the top surface of the needle base 252 are illustrated as substantially planar with the tip portions of the needles 102 positioned on a 2D or common plane, it shall be understood that the shape of needle base 252 and/or length of the needles 102 can vary, such that the tip portions of the needles are non-planar and provide a curved fluid distribution system. For example, the needle base 252 can comprise a saddle-shape with the tip portions of each needle positioned at points along a curved plane. In another example, the needle base 252 can be substantially planar with the plurality of needles 102 having different lengths, such that the tip portions of each needle are positioned at points along a curved plane.

Referring to FIG. 3B, the needle base 252 can comprise needle apertures 256 that are in fluid communication with each of the needles 102. The apertures 256 can extend from the bottom surface to the top surface of the needle base 252 to permit a medicament to be directed through the needle base 252 to each needle 102. Each aperture 256 comprises a cross-sectional inner profile that defines the size of the aperture. The size of the aperture can be configured to regulate a flow rate and/or volume of a medicament that is directed into each respective needle 102. The needle base 252 can comprise apertures 256 having substantially the same size to provide an even or balanced ejection of medicament from the needles. The apertures, in some embodiments, can have different sizes to provide an even or balanced ejection of medicament from the needles when a fluid path to one or more needle 102 comprises different features, such as length, width, or cross-sectional profile.

The needle assembly 108 can comprise coupling members and orientation features to facilitate coupling between portions of the needle array device 100. To couple the needle assembly 108 with the sleeve 106, the needle base 252 can comprise a clip 258. In some examples, two clips 258 extend from the top surface at opposite sides of the needle base 252. The clips 258 can comprise an interface surface having a protrusion 260 configured to engage another portion of the needle array device 100.

The outer surface of the sleeve 106 comprises a coupling channel 262 configured to receive the clip 258 therein when the sleeve 106 is coupled with the needle base 252. The channel 262 can include a ridge 264 configured to retain the sleeve 106 with the needle base 252, and resist separation or movement of the sleeve 106 away from the needle base 252.

When the sleeve 106 is coupled with the needle base 252, the protrusion 260 can extend over or past the ridge 264 to engage against the ridge 264. Any of the clip 258, the protrusion 260, the channel 259, and the ridge 264 can be flexible to permit separation of the sleeve 106 from the needle base 252. For example, the clips 258 can be urged away from an outer surface of the sleeve 106 to couple the needle assembly 108 with the sleeve 106, and can be urged away from the outer surface of the sleeve 106 to separate the needle assembly 108 from the sleeve 106.

In some embodiments, the support base 110 and/or the sleeve 106 can comprise a clip 258 configured to engage the other of the support base 110 and the sleeve 106. When the support base 110 and the sleeve 106 are coupled together, the needle base 252 can be retained therebetween.

To facilitate orientation of the needle assembly 108 with another portion of the needle array device 100, the needle base 252 can comprise an orientation feature. The orientation feature can include any of a notch, aperture, pin, and ridge, or combination thereof. Referring to FIGS. 3A and 3B, notches 266 extend from opposing outer side surfaces into the needle base 252. The notches 266 are configured to receive a ridge 268 that extends from the support base 110. In some embodiments, the orientation feature includes an aperture that extends through the needle base 252. The aperture 270 is configured to receive a locating pin 272 that extends from the support base 110. The position of one or more aperture 270 and locating pin 272 limits the potential orientation of the needle base 252 relative to the support base 110 when the needle base 252 and support base 110 are coupled together.

Figure 4:
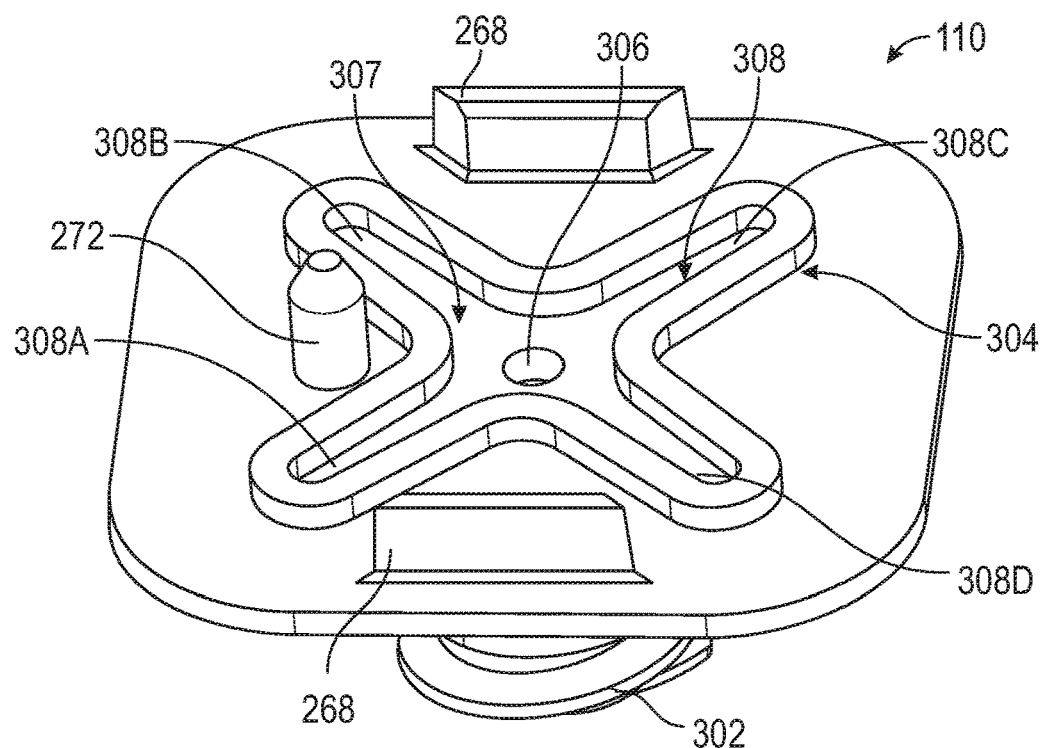
FIG. 4 is an isolated perspective view of a support base of the needle array device of FIGS. 1-3B, according to some embodiments.

Referring now to FIGS. 3B and 4, the needle array device 100 includes a support base 110 configured to couple to the needle assembly 108. The support base 110 comprises a Luer connector 302 for coupling to a syringe device, and a fluid manifold 304 defining a fluid pathway for directing a medicament between the Luer connector 302 and the plurality of needles 102. In some embodiments, the support base 110 comprises an upper portion comprising the fluid manifold 304, and a lower portion comprising the Luer connector 302.

The Luer connector 302 comprises an entrance aperture 303 extending through the Luer connector 302 toward the fluid manifold 301, and defining a fluid pathway between the Luer connector 302 and the fluid manifold 301. The Luer connector 302 can be configured to couple with a 0.8 mL or 1 mL syringe manufactured by Allergan plc of Dublin, Ireland. The Luer connector 302 can comprise features disclosed in International Patent Application No. PCT/US2009/066427, the disclosure of each of which is incorporated herein by reference in its entirety for all purposes.

The upper portion of the support base 110 can be coupled to the lower portion of the needle base 252 to form a fluid distribution cavity therebetween. When the support base 110 and the needle base 252 are coupled together, the entrance aperture 303 and each of the plurality of needle apertures 256 are fluidly coupled with the fluid distribution cavity.

The fluid manifold 304 comprises an inflow aperture 306 and flow channels 308. Four flow channels 308A, 308B, 308C, and 308D extend away from the inflow aperture 306. However, it should be understood that one or more flow channel 308 can be oriented in any direction and/or configuration fluidly coupled with the inflow aperture 306.

The inflow aperture 306 is fluidly coupled with the Luer connector 302 and the flow channels 308, such that a volume of a syringe coupled to the needle array device 100 is in fluid communication with the flow channels 308. The fluid manifold 304 defines a portion of defines or forms a portion of the fluid distribution cavity. In some embodiments, the fluid manifold 304 forms the side walls of the fluid distribution cavity, an upper surface of the support base 110 forms the bottom surface of the fluid distribution cavity, and a bottom surface of the needle base 252 forms fluid distribution cavity.

The flow channels 308 form a fluid pathway that directs a fluid from inflow aperture 306 toward the needle apertures 256. The flow channels 308 can divide or branch the fluid pathway from inflow aperture 306 toward one or more of the plurality of needles 102. The flow channels 308 comprise a profile and form a boundary pattern to enable a medicament to be driven uniformly and arrive at all the apertures of the tip portions of the needles 102 approximately simultaneously, such that the medicament is ejected from all needles 102 approximately at same time, same pressure, and/or same volume. As a result, some embodiments can advantageously ensure that there is a low dosage discrepancy between the needles (e.g., that the dosage or fluid outflow from each of the needles is approximately equal) when medicament or fluid is ejected therefrom.

The flow channels 308 can be formed as concave portions or a groove that extends into a surface of the support base 110. Referring to FIG. 4, the flow channels 308 are formed by walls that extend from a top surface of the support base 110. A bottom surface and perimeter of the flow channels 308 can be defined by the support base 110, and a top surface of the flow channels 308 can be formed by the needle base 252 when the support base 110 is coupled with the needle assembly 108. In some examples, the flow channels 308 can be formed by a bottom portion or surface of the needle base 252.

Each flow channel 308 can define a pathway that extends from the inflow aperture 306 to one or more needle 102. In some examples, the flow channel 308 can comprise a first portion and a second portion that comprises branches. The first portion extends from the inflow aperture 306 toward the second portion of the flow channel 308. The second portion of the flow channel 308 comprises branches that extend away from the first portion. Each branch can extend from the first portion of the flow channel 308 toward one or more of the needles 102.

In some examples, the fluid manifold 304 can comprise one or more passages that extend through the support base 110. For example, the fluid manifold 304 can comprise a passage that extends from the Luer connector 302 to each of the plurality of needles 102. For example, the fluid manifold 304 comprises an inflow aperture that extends through the support base 110.

The inflow aperture 306 extends through the support base 110 to provide a passage from the Luer connector 302 to the flow channels 308. The flow channels 308 extend outward from the inflow aperture 306 toward the needles 102 so that a single stream of a medicament is diverted into multiple streams. For example, a single stream of a medicament directed through the inflow aperture 306 enters the fluid manifold 304 and is then diverted to each flow channel 308.

The inflow aperture 306 is positioned to enable use with a particular needle array arrangement or is positioned adjacent to or coupled with the Luer connector 302. The inflow aperture 306 can be positioned in a center of the support base 110 or offset from the center of the support base 110. Referring to FIG. 4, the inflow aperture 306 is positioned at the approximate center of the support base 110 with each of the flow channels 308 extending symmetrically outward from the inflow aperture 306. However, the inflow aperture 306 can be positioned offset from the center of the support base 110 with flow channels 308 extending from the offset inflow aperture 306 toward each needle 102.

Each flow channel 308 forms a shape that includes a length and a cross-sectional profile. The flow channel 308 comprises a plurality of flow channels or area having a width and/or depth. The cross-sectional profile can be oriented transverse to the length of the flow channel 308. The cross-sectional profile or shape of the flow channel 308 can be configured for the medicament to be ejected from all needles 102 approximately at same time, same pressure, and/or same volume.

The length of each flow channel 308 can extend from a proximal portion at the inflow aperture 306 to a distal portion where the fluid passageway extends from the flow channel 308 to a needle 102. The length of the flow channel 308 can refer to a length of a fluid path between the inflow aperture 306 and an aperture 256 of the needle base 252. In some embodiments, the length of each flow channel 308 can define a length of the fluid pathway from the inflow aperture 306 to the needles 102.

To cause a medicament to be ejected from all needles 102 at approximately the same time, same pressure, and/or same volume, each flow channel 308 can have approximately the same length. Where the distance between the inflow aperture 306 and the apertures 256 is the same for each of the needles 102, each flow channel 308 can have the same length. The approximately equal length or distance of the fluid path can cause a fluid to reach tips of the needles 102 approximately simultaneously, thus tending to ensure a low dosage discrepancy.

In some embodiments, each flow channel 308 can extend symmetrically from the inflow aperture 306 to the needles 102. However, where the distance between the inflow aperture 306 and the apertures 256 is different for some of the needles 102, one or more flow channel 308 can have the same length and extend along a tortuous path.

In some embodiments, the length of the fluid path from the inflow aperture 306 to a first needle aperture is approximately equal to a length of the fluid path from the inflow aperture 306 to a second needle aperture. The approximately equal lengths of the fluid paths can cause a fluid to reach tips of the first and second needles 102 approximately simultaneously. Such embodiments can be used to deliver a fluid simultaneously to tips of the needles when the needles are the same length as each other.

However, in some embodiments, the needles may have differing lengths, which would require the fluid to be distributed through the flow channels and reach needle apertures at different moments (e.g., before or after fluid reaches other needle apertures) so that the fluid can reach the tips of all of the needles approximately simultaneously. For example, in some embodiments, the length of the fluid path from an inflow aperture to a first needle aperture may be different than a length of the fluid path from the inflow aperture to a second needle aperture. The different lengths of the fluid path can cause a fluid to reach the needle apertures at different moments, but can ensure that the fluid reaches the tips of the first and second needles approximately simultaneously. Further, other aspects of the fluid paths can be modified, such as the volume or cross-sectional shape to tend to cause the fluid to reach the needle apertures at different moments and cause the fluid to reach the needle tips approximately simultaneously.

The cross-sectional profile or shape of the flow channels 308 can be configured to cause a medicament to be ejected from all needles 102 at approximately the same time, same pressure, and/or same volume. The cross-sectional profile of the flow channels 308 can be uniform or varied along the fluid pathway, thereby effecting flow characteristics of a medicament.

To increase a resistance to medicament flow through a portion of the fluid pathway, a flow channel 308 may comprise a portion having a reduced cross-sectional profile relative to other portions of the flow channel 308 or other flow channels 308. The reduced cross-sectional profile of the flow channel 308 can increase resistance and/or pressure along a length of the fluid path.

A flow channel 308 can have a smaller cross-sectional area than the reservoir 307 for increasing the flow resistance through the flow channel 308. In some embodiments of the present disclosure, the width of the reservoir 307 is at least twice as large as a width of the flow channels 308. In some embodiments, each of the flow channels 308 has an approximately constant cross-sectional area.

In contrast, to reduce resistance to medicament flow, a flow channel may comprise a portion having a larger cross-sectional profile relative to other portions of the flow channel 308 or other flow channels 308.

The fluid path from the inflow aperture 306 to each needle aperture 256 or needle 102 can comprise a pathway volume. The pathway volume of each fluid path can be defined by the cross-sectional profile or shape of each flow channel. The cross-sectional profile or shape of each flow channel can include any of the length, the width, and the depth of the respective flow channel. Optionally, the pathway volume can also include the volume of the fluid reservoir. However, the pathway volume can be defined as the volume of the flow channel along which the fluid path extends from the fluid reservoir to the respective flow channel outlet end.

To cause a medicament to be ejected from all needles 102 at approximately the same time, same pressure, and/or same volume, the pathway volume of the fluid path or flow channel 308 can be approximately equal. In accordance with some embodiments, the pathway volumes of the fluid pathways of a support base can be approximately equal to each other. By "approximately equal," the pathway volumes can have respective volumes that are within about 20% of each other, about 15% of each other, about 12% of each other, about 10% of each other, about 8% of each other, about 6% of each other, about 4% of each other, or about 2% of each other. In some embodiments, the largest and the smallest pathway volumes of all of the fluid pathways of a support base can be approximately equal to each other.

In some embodiments, a fluid path from the inflow aperture 306 to a first needle aperture comprises a first pathway volume, and a fluid path from the inflow aperture 306 to a second needle aperture comprises a second pathway volume. To cause a medicament to be ejected from all needles 102 approximately equally, or at approximately the same time, same pressure, and/or same volume, the first pathway volume can be approximately equal to or different than the second pathway volume, depending on needle length.

In some embodiments of the present disclosure, the fluid reservoir 307 comprises a volume. The volume of the fluid reservoir 307 can optionally be larger than the volumes of each of the plurality of flow channels 308. As a general principle, fluid will flow in the direction of least resistance, thus filling areas of the fluid reservoir or flow channels that offered the lowest degree of resistance to fluid flow. As the volume of medicament accumulating in the fluid reservoir 407 increases, some of the medicament will begin to be directed into one or more flow channels 308. Thus, the larger volume of the fluid reservoir 307, relative to each of the plurality of flow channels 308, permits a fluid or medicament to accumulate in the fluid reservoir 307 and move toward each of the flow channels 308 before moving into and along the plurality of flow channels 308 toward a needle aperture 256. Accumulation of the medicament in the fluid reservoir 307 can facilitate ejection of the medicament from all needles 102 approximately equally, or at approximately the same time, same pressure, and/or same volume.

To achieve ejection of a medicament from all needles 102 at approximately the same time, same pressure, and/or same volume, any combination of flow channel 308 length and cross-sectional profile can be implemented. In some examples, the flow channel 308 can comprise additional or alternative features, structures, or surface finishes that can affect flow characteristics of a medicament. The flow channel 308 orientation and pattern can comprise any shape consistent with achieving the distribution of a medicament to the needles 102. One or more flow channel 308 pattern is possible with a particular needle arrangement pattern. For example, a 2×2 needle arrangement array can comprise flow channels 308 forming an "X" shape. In some embodiments of the present disclosure, the flow channels 308 form or a zig-zag shape or concentric spirals similar to a camera aperture.

The fluid manifold 304 can comprise a fluid reservoir 307 between the inflow aperture 306 and the flow channels 308. The fluid reservoir 307 is configured to receive a medicament from the inflow aperture 306 and provide a cavity where the medicament can accumulate and move into the flow channels 308.

The position of the fluid reservoir 307 and the inflow aperture 306 are aligned relative to each other so that the fluid reservoir 307 is in fluid contact with the inflow aperture 306. The fluid reservoir and the inflow aperture 306 can be positioned with the inflow aperture 306 in a center of the fluid reservoir 307. In some embodiments, the fluid reservoir 307 and the inflow aperture 306 are positioned with the inflow aperture 306 offset from a center of the fluid reservoir 307.

The fluid reservoir 307 can be formed as a portion of the flow channels 308 or as a separate cavity that is fluidly coupled with the flow channels 308. The fluid reservoir 307 can be formed by proximal portions of the flow channels 308 that intersect or are coupled together. The flow channels 308 can extend from the fluid reservoir toward the needles 102. In some examples, the fluid reservoir 307 can be formed by a portion of the flow channel that comprises an increasing and/or decreasing cross-sectional profile.

Referring to FIG. 4, the fluid reservoir 307 and the inflow aperture 306 are positioned in a center of the support base 110. The fluid reservoir 307 is formed by proximal portions of the flow channels 308 that are coupled together to form a closed cavity. The width of the flow channels 308 narrows or tapers away from fluid reservoir 307 toward a distal portion of each flow channel 308.

The flow channels 308 can extend in a direction away from the inflow aperture 306. The flow channels 308, illustrated in FIGS. 4 and 5, form an X-shape or cross-shape pattern with the reservoir 307 being disposed at a central position of the cross-shaped pattern.

In some embodiments, the needle array device 100 can comprise two or more fluid reservoirs 307. The needle array device 100 can comprise two fluid reservoirs 307, each fluidly coupled with a group of flow channels 308. Where the flow channels 308 comprise one or more branches, the one or more branches can comprise a fluid reservoir 307. In some examples, a fluid reservoir can be positioned along one or more flow channel 308.

Figure 5:
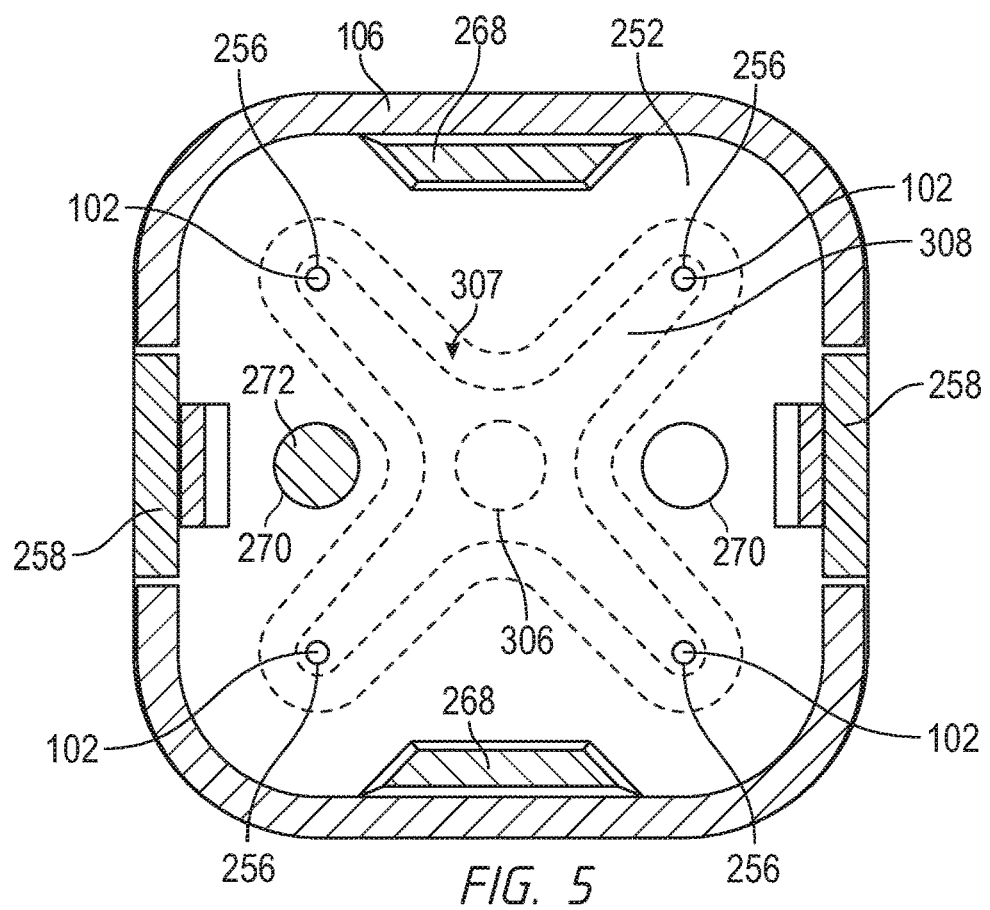
FIG. 5 is a bottom cross-section view of a needle array device along the line 5-5 of FIG. 1, according to some embodiments.

Referring to FIG. 5, a cross-sectional view of the needle array device 100 through line 5-5 of FIG. 1 illustrates the fluid distribution system. The fluid distribution system includes the fluid manifold 304 formed by the flow channels 308 of the portions of the support base 110 and the needle base 252 of the needle assembly. The flow channels 308 and the inflow aperture 306 are illustrated in hash-lines to indicate the location of the inflow aperture 306 relative to the fluid reservoir 307, the flow channels 308, apertures 256, and needles 102.

The inflow aperture 306 and fluid reservoir 307 are centrally located with the flow channels 308 extending from the fluid reservoir 307 to the apertures 256. When a medicament is directed into the fluid distribution system through the inflow aperture 306, the medicament can accumulate in the fluid reservoir. As the volume of medicament accumulating in the fluid reservoir increases, some of the medicament will be directed into one or more flow channel 308. Because the fluid reservoir 307 comprises a cavity having a larger cross-sectional profile, relative to the flow channels 308, the medicament can be distributed to each of the remaining empty flow channels 308.

The flow of a medicament through the fluid distribution system is illustrated in FIGS. 6A-6D, which illustrate different stages of the movement and distribution of a medicament M relative to the needles 102, the apertures 256, the inflow aperture 306, the fluid reservoir 307, and the flow channels 308.

Figure 6A:
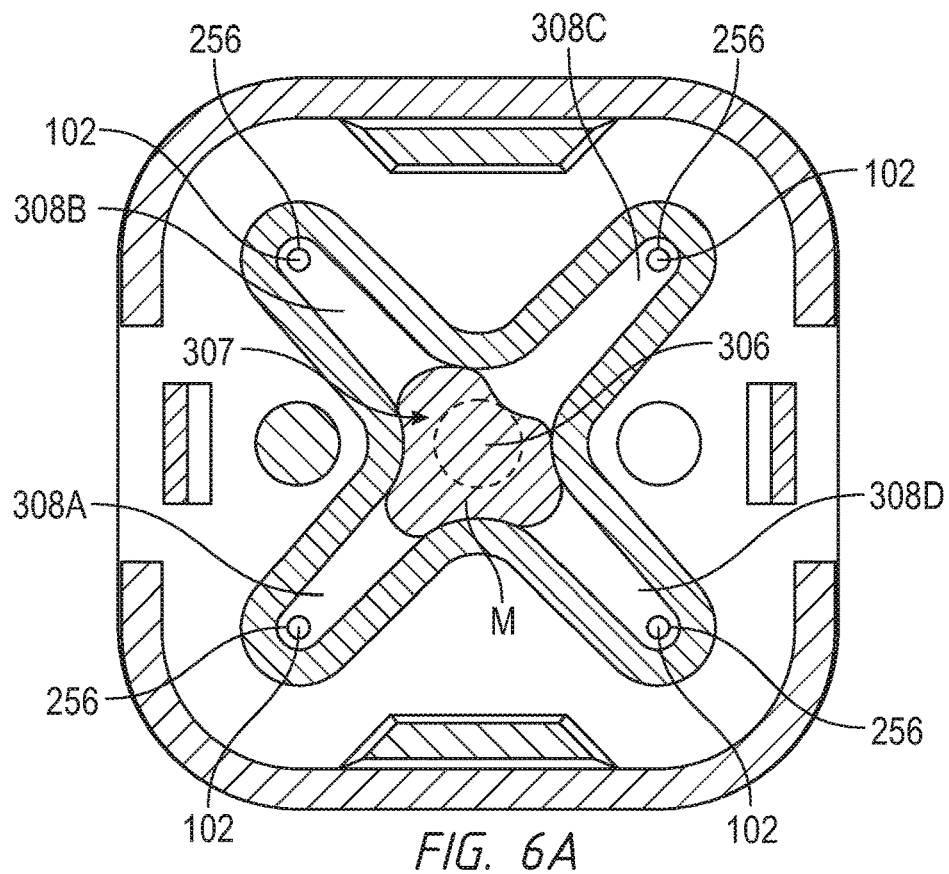
FIGS. 6A-6D are bottom cross-section views of a needle array device, according to some embodiments.

FIG. 6A illustrates the medicament M directed from the inflow aperture 306 (shown in hashed-lines) into a fluid reservoir 307. Flow channels 308 extend from the fluid reservoir to the apertures 256. Because the fluid reservoir 307 comprises a larger cross-sectional profile or width, relative to the cross-sectional profile or width of the flow channels 308, the resistance to flow within the fluid reservoir 307 is minimal. In the fluid reservoir 307, the medicament M accumulates in the fluid reservoir 307 and the outer edge or boundary layer of the medicament M begins to flow toward the flow channels 308.

Figure 6B:
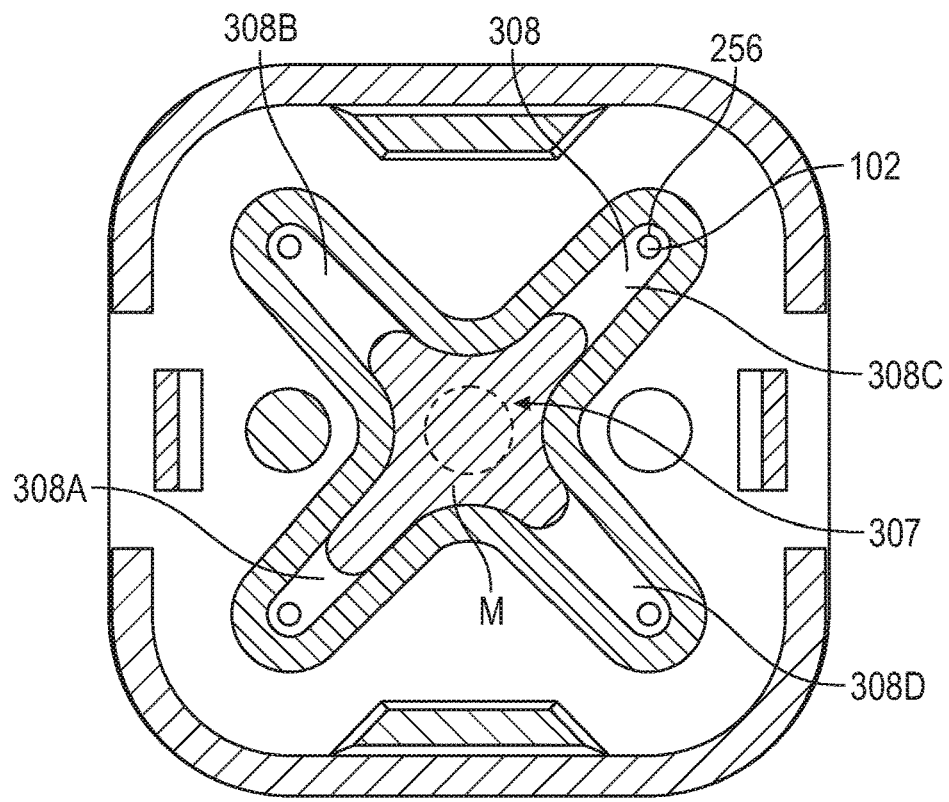

In FIG. 6B, the medicament M has fully filled the fluid reservoir 307 and a portion of the medicament M has flowed into at least one flow channel 308A. Because the flow channel 308A has a greater resistance to flow, relative to the fluid reservoir 307, additional medicament M directed into the fluid reservoir 307 can move toward the other flow channels 308B, 308C, and 308D. As the medicament M is directed into the fluid reservoir 307, the boundary layer moves toward the needles 102 at a distal portion of each flow channel 308A, 308B, 308C, and 308D.

Figure 6C:
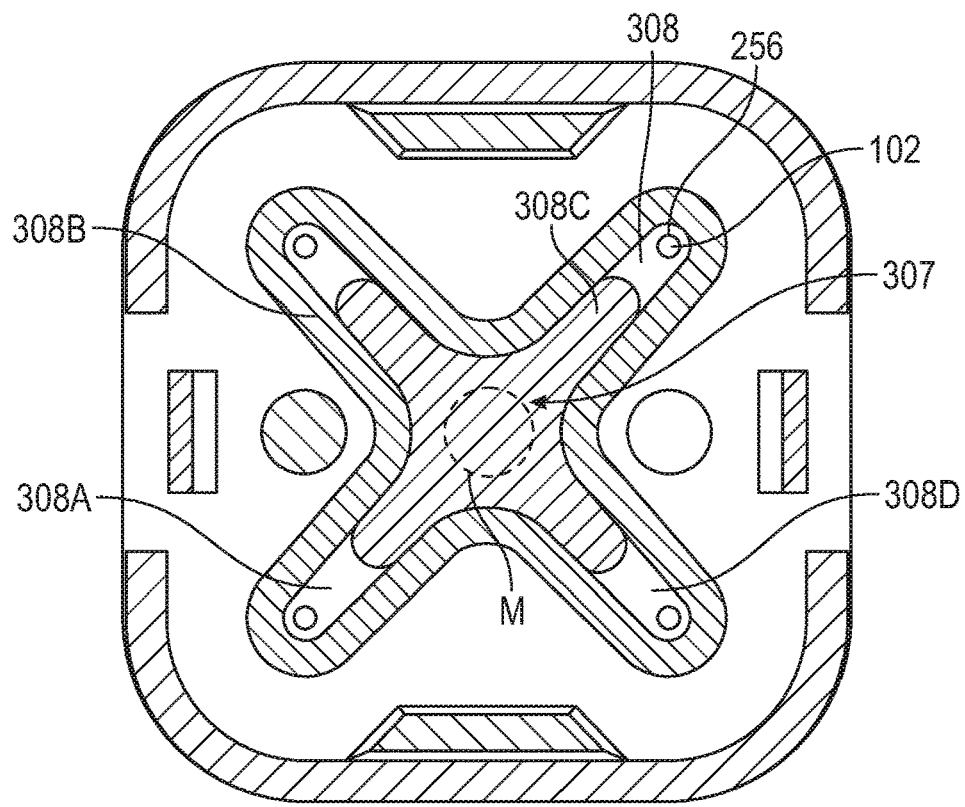

Referring now to FIG. 6C, the boundary layer of the portion of the medicament M that entered the flow channel 308A in FIG. 6B has remained stationary due to an increasing resistance to flow along the length of the flow channel 308A. The increased resistance to flow at a distal portion of the flow channel 308A, and the accumulation of medicament M in the fluid reservoir, cause the medicament M to move toward a path of lesser resistance. Accordingly, a portion of the medicament M has now flowed into each of the flow channels 308B, 308C, and 308D.

Figure 6D:
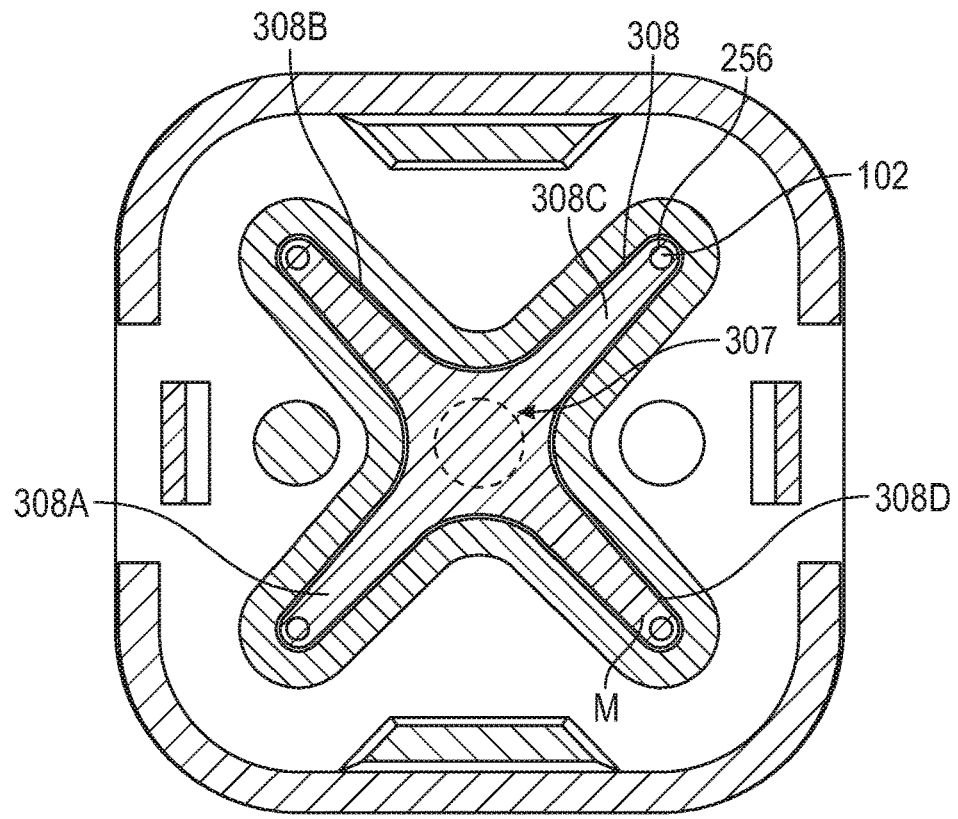

At FIG. 6D, the medicament M is evenly distributed between the inflow aperture 306 and the aperture 256 of each flow channel 308A, 308B, 308C, and 308D. Because the medicament M is evenly distributed in the flow channels 308A, 308B, 308C, and 308D, additional medicament M directed into the fluid distribution system will cause medicament M to move through the aperture 256 to the needles 102 to be ejected from all needles 102 at approximately at same time, same pressure, and/or same volume.

To determine the amount or volume of medicament ejected using the needle array device 100, the amount of medicament ejected from a syringe coupled to the needle array device 100 can be divided by the number of needles 102. For example, if 40 µL of medicament is ejected from the syringe, and if the needle array device 100 comprises four needles 102, each needle 102 could have ejected 10 µL of medicament.

Figure 7:
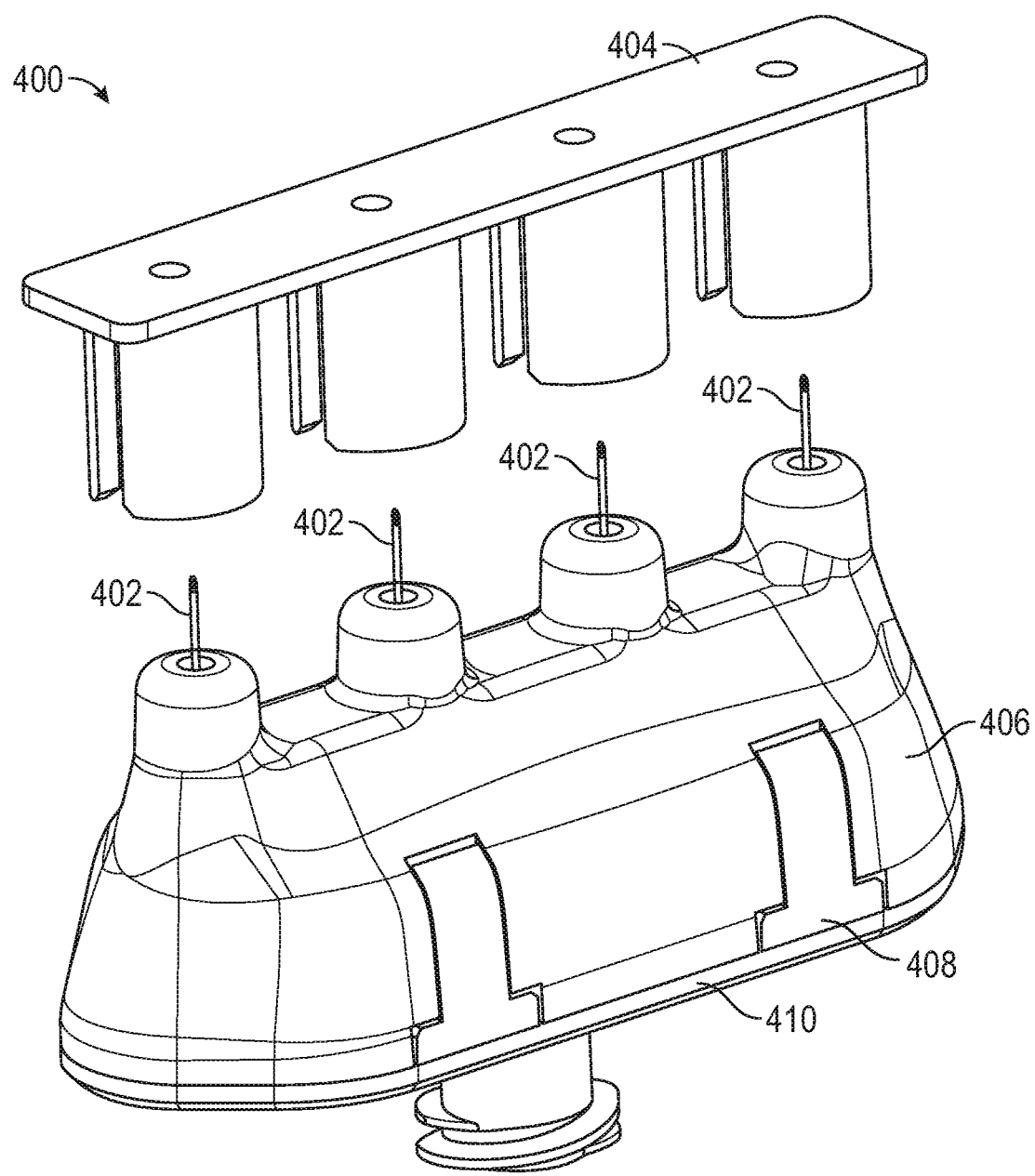
FIG. 7 is a front perspective view of a 1×4 needle array device, according to some embodiments.
Figure 8:
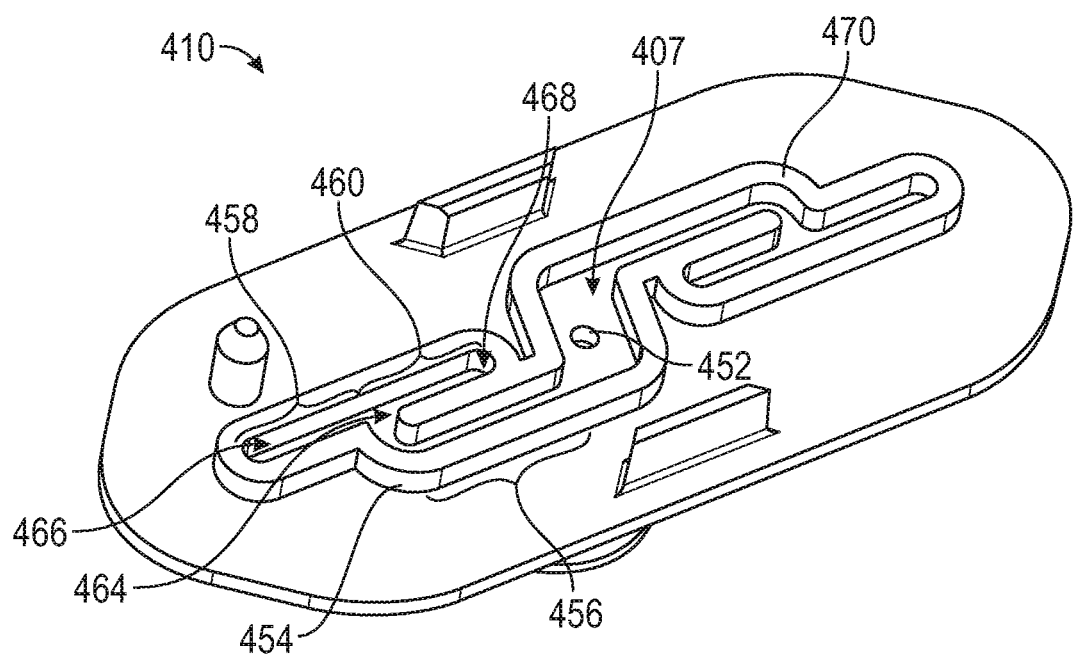
FIG. 8 is an isolated perspective view of a support base of the needle array device of FIG. 7, according to some embodiments.

Referring now to FIGS. 7 and 8, an embodiment of a needle array device 400 comprising four needles arranged in a 1×4 pattern is illustrated. The needle array device 400 comprises general features of the 2×2 needle arrangement pattern illustrated in FIGS. 1-6, and includes a plurality of needles 402, a removable protector 404, a sleeve 406, a needle assembly 408, and a support base 410. The general features of the needle array device 400 in common with the needle array device 100 are not repeated here for clarity and brevity, but are incorporated here by reference.

The support base 410, illustrated in FIG. 8, comprises a fluid distribution system configured to distribute a medicament to the needle array device 400 comprising a 1×4 needle arrangement pattern. The support base 410 comprises a fluid pathway for directing a medicament between a Luer connector and the plurality of needles 402.

The support base 410 comprises an inflow aperture 452, a fluid reservoir 407, and flow channels 454. The inflow aperture 452 and fluid reservoir 407 can be positioned at an approximate center of the support base 410 with the flow channels 454 extending from the fluid reservoir 407. Some features and characteristics of the fluid distribution system that dictate the flow of a medicament are the same as those discussed elsewhere in this application. Accordingly, some common features and characteristics are not repeated here for clarity and brevity, but are incorporated here by reference.

Each flow channel 454 can comprise a shared portion or segment 456 and a plurality of terminal portions or segments 458, 460. FIG. 8 shows two terminal segments 458, 460 splitting from an end of the shared segment 456; however, more than two terminal segments can split from the shared segment 456 in some embodiments. The shared segment 456 extends away from the fluid reservoir 407 toward the terminal segments 458, 460. The flow channel 454 can branch into the terminal segments 458, 460 to divide the flow channel 454 from a single fluid path (i.e., the shared segment 456) into two fluid paths (e.g., terminal segments 458, 460).

Each terminal segment 458, 460 can comprise an inlet portion that is in fluid communication with a terminal end 464 of the shared segment 456. Further, each terminal segment 458, 460 can also comprise an outlet end 466, 468 that is in fluid communication with a respective needle aperture or needle. The outlet end 466, 468 of each of the terminal segments 458, 460 can form an end point of the flow channel 454. The outlet end 466, 468 of the terminal segments 458, 460 is positioned at a location where a needle 402 is fluidly coupled with the fluid distribution system. In some embodiments, the outlet end 466, 468 is aligned approximately with the needle aperture of the needle base. The outlet end 466, 468 of each of the terminal segments 458, 460 can be aligned along a straight line extending through each of the terminal segments 458, 460.

Each fluid path can extend between the inflow aperture 452 and one or more flow channel outlet ends. A fluid path can comprise the shared segment 456 and a plurality of terminal segments 458, 460 of the flow channel. For example, the plurality of terminal segments can comprise two, three, four, or more terminal segments. Because fluid paths toward each of the respective needles can be branched away from other fluid paths in accordance with some embodiments, at least a portion of a fluid path toward a given needle can be shared with another fluid path. For example, a first fluid path can comprise the shared segment 456 in combination with the terminal segment 458, and a second fluid path can comprise the same shared segment 456 in combination with the terminal segment 460.

Further, in accordance with some embodiments, each fluid path can terminate at an outlet end. As illustrated, the first flow path can terminate in a first outlet end 466, and the second flow path can terminate in a second outlet end 468.

In accordance with some embodiments, any of the support bases disclosed herein can be configured to include one, two, or more flow channels. For example, the support base 110 comprises four flow channels. Further, the support base 410 can include a second flow channel 470. Moreover, support base 510 (shown in FIG. 10 and discussed further below) comprises three flow channels. Flow channels of any of the embodiments disclosed herein, such as the support base 110, the support base 410, and/or the support base 510 can include flow channels that include features such as those discussed with respect to the flow channel 454.

For example, the second flow channel 470 of the support base 410 in FIG. 8 can comprise the features discussed with reference to flow channel 454, including a shared segment having a terminal end, as well as terminal segments having outlet ends. The features of the second flow channel 470 in common with the flow channel 454 are not repeated here for clarity and brevity, but are incorporated here by reference. The features of flow channel 454 can also be applied to other embodiments of the present disclosure, including embodiments shown in FIGS. 1 and 10.

Moreover, the support base of any of the embodiments disclosed herein can comprise flow channels having multiple fluid paths. Each fluid path can lead from an inflow aperture or fluid reservoir toward a respective needle aperture. Thus, for example, the support base 110 comprises four fluid paths that each lead to a respective needle aperture, the support base 410 also comprises four fluid paths that each lead to a respective needle aperture, and the support base 510 comprises six fluid paths that each lead to a respective needle aperture.

In accordance with some embodiments, each fluid path can have a length, which can be measured as the distance within the flow channel between the inflow aperture and the flow channel outlet end. The length can be a direct or shortest distance between the inflow aperture and the outlet end. For example, as illustrated in FIG. 8, the length of the first fluid path (the combination of the shared segment 456 and the terminal segment 458) can be the shortest path through the flow channel 454, between the inflow aperture 452 to the flow channel outlet end 466. In some embodiments, the length of a fluid path includes a length between the inflow aperture and the aperture of the needle base or the needle.

Each fluid path can comprise a pathway volume. The pathway volume can include portions of the flow channel. Optionally, the pathway volume can also include the volume of the fluid reservoir. However, the pathway volume can be defined as the volume of the flow channel along which the fluid path extends from the fluid reservoir to the respective flow channel outlet end.

For example, the first fluid path can define a first pathway volume, which can be the summation of the volume of the shared segment 456 and the volume of the terminal segment 458. Similarly, the second fluid path can define a second pathway volume, which can be the summation of the volume of the shared segment 456 and the volume of the terminal segment 460. Thus, in determining a pathway volume of a fluid path, multiple fluid paths may have a volume that is based on a volume of a common or shared portion of a flow channel or fluid reservoir.

In accordance with some embodiments, the pathway volumes of the fluid pathways of a support base can be approximately equal to each other. By "approximately equal," the pathway volumes can have respective volumes that are within about 20% of each other, about 15% of each other, about 12% of each other, about 10% of each other, about 8% of each other, about 6% of each other, about 4% of each other, or about 2% of each other. In some embodiments, the largest and the smallest pathway volumes of all of the fluid pathways of a support base can be approximately equal to each other.

With continued reference to FIG. 8, in some embodiments, the shared segment 456 of the flow channel can define a shared pathway volume, and the terminal segments 458, 460 of the flow channel can each define a respective terminal pathway volume. The shared pathway volume can be approximately equal to the terminal pathway volume. However, in some embodiments of the present disclosure, the terminal pathway volume of the flow channel can be less than the shared pathway volume of the flow channel. The shared pathway volume and the terminal pathway volume can be less than a volume of the fluid reservoir 407. The relative pathway volumes of a fluid path can provide resistance to medicament flow through the fluid distribution system. As a medicament is directed along a fluid path, resistance to movement of the medicament can be greater along the shared segment 456 of the flow channel relative to the fluid reservoir 407. A resistance to movement of the medicament can also be greater along the terminal segments 458, 460 relative to the shared segment 456. Thus, a decreasing pathway volume along a fluid path can create an increasing degree of resistance to fluid travel as the fluid moves further along the fluid path, such as when the fluid reaches the reaches the shared segment and/or terminal segments. In some embodiments, such configurations can advantageously facilitate an objective of the present disclosure, which is to tend to ensure that fluid is delivered to each of the needle tips approximately simultaneously, thus tending to ensure a low dosage discrepancy.

For example, when a medicament is directed into the fluid distribution system through the inflow aperture 452, the medicament can accumulate in the fluid reservoir 407. As a general principle, the fluid will flow in the direction of least resistance, thus filling areas of the fluid reservoir or flow channels that offered the lowest degree of resistance to fluid flow. As the volume of medicament accumulating in the fluid reservoir 407 increases, some of the medicament will begin to be directed into one or more flow channels 454, 470. Because the fluid reservoir 407 comprises a cavity having a larger cross-sectional profile than the flow channels 454, 470, the medicament will tend to be distributed toward all of the flow channels 454, 470 before advancing into or far along the flow channels 454, 470. Resistance to flow along any of the shared segment and the terminal segments, as well as the accumulation of medicament in the fluid reservoir, can cause the medicament to move into and evenly fill the flow channels 454, 470. With medicament evenly distributed in the flow channels 454, 470, additional medicament directed into the fluid distribution system will cause the medicament to move through the needles 402 to be ejected from all needles 402 at approximately at same time, same pressure, and/or same volume. Further, in some embodiments where the needles have different lengths, the configuration of the flow channels can be modified to ensure that fluid reaches outlet ends of the flow channels at different moments to tend to ensure that the fluid reaches the tips of the needles approximately simultaneously.

The fluid reservoir 407 comprises a larger cross-sectional profile or width, relative to the cross-sectional profile or width of the shared segment 456 of the flow channel 454. In some embodiments, the shared segment 456 comprises a larger cross-sectional profile or width, relative to the cross-sectional profile or width of the terminal segments 458, 460 of the flow channel. In some examples of the present disclosure, the cross-sectional profile or width of the fluid reservoir 407, and/or the cross-sectional profile or width of the flow channels 454, 470, can taper from the inflow aperture 452 toward the outlet end 466, 468 of each of the terminal segments 458, 460.

Figure 9:
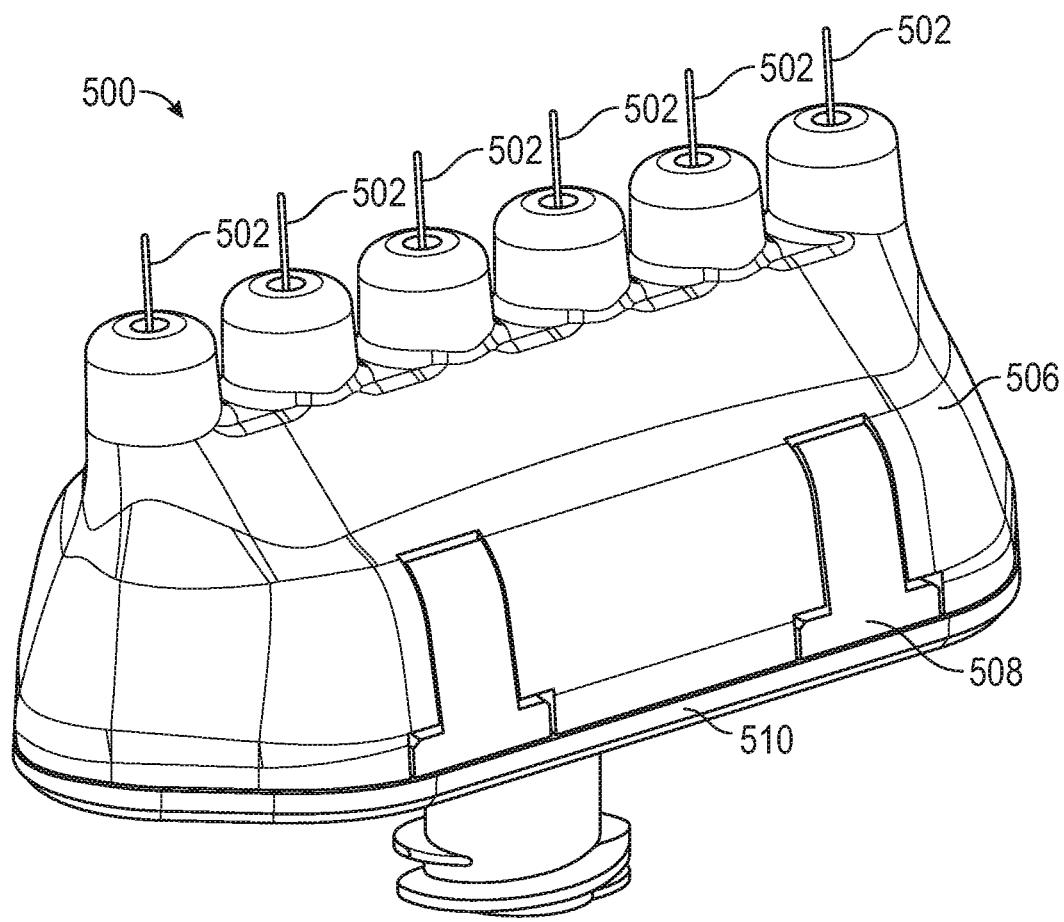
FIG. 9 is a front perspective view of a 1×6 needle array device, according to some embodiments.
Figure 10:
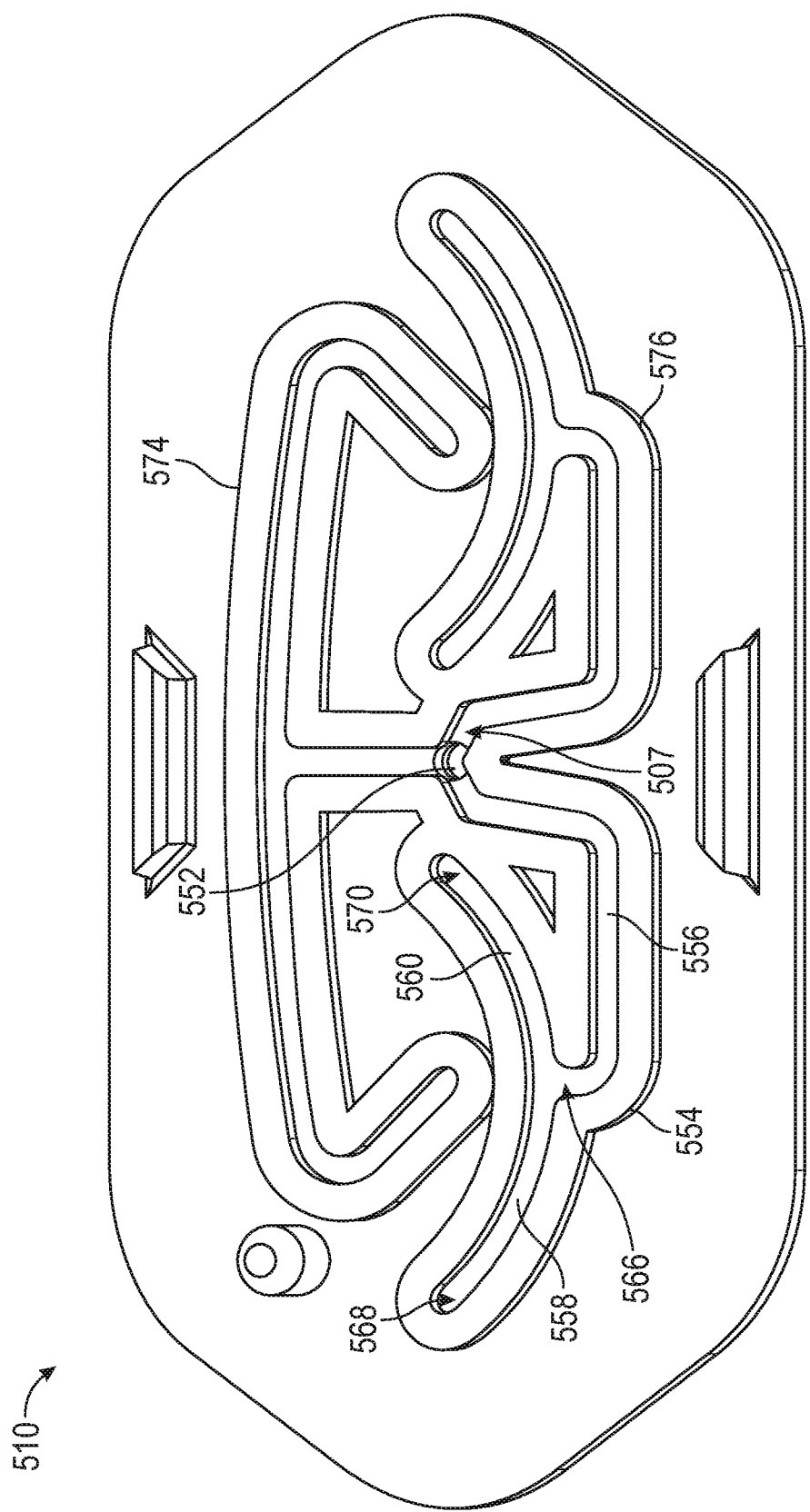
FIG. 10 is an isolated perspective view of a support base of the needle array device of FIG. 9, according to some embodiments.

Referring now to FIGS. 9 and 10, an embodiment of a needle array device 500 comprising six needles arranged in a 1×6 pattern is illustrated. The needle array device 500 comprises features of the 2×2 and 1×4 needle arrangement pattern illustrated in FIGS. 1-8. The needle array device 500 can include a plurality of needles 502, a removable protector, a sleeve 506, a needle assembly 508, and a support base 510. Some features of the needle array device 500, which can be in common with the needle array device 100 and 400, are not repeated here for clarity and brevity, but are incorporated here by reference.

The support base 510, illustrated in FIG. 10, comprises a fluid distribution system configured to distribute a medicament to the needle assembly 508 comprising the 1×6 needle arrangement pattern. The support base 510 comprises a fluid pathway for directing a medicament between a Luer connector and the plurality of needles 502.

The support base 510 can comprise an inflow aperture 552, a fluid reservoir 507, and a flow channel 554. The inflow aperture 552 and fluid reservoir 507 are positioned at an approximate center of the support base 510 with the flow channel 554 extending from the fluid reservoir. Some features and characteristics of the fluid distribution system that dictate the flow of a medicament are the same as those discussed elsewhere in this application, including the fluid distribution systems discussed with reference to FIGS. 1 and 7. Accordingly, some common features and characteristics are not repeated here for clarity and brevity, but are incorporated here by reference.

Therefore, similar to the flow channel 454 discussed above, the flow channel 554 can comprise a shared segment 556 and a plurality of terminal portions or segments 558, 560. The shared segment 556 extends away from the fluid reservoir 507 toward the respective terminal segments 558, 560. The flow channel 554 can branch into the terminal segments 558, 560 to divide the flow channel 554 from a single fluid path (i.e., the shared segment 556) into two fluid paths (e.g., terminal segments 558, 560).

Each terminal segment 558, 560 can comprise an inlet portion that is in fluid communication with a terminal end 566 of the shared segment 556. Further, each terminal segment 558, 560 can also comprise an outlet end 568, 570 that is in fluid communication with a respective needle aperture or needle. The outlet end 568, 570 of each of the terminal segments 558, 560 can form an end point of the flow channel 554. The outlet end 568, 570 of the terminal segments 558, 560 is positioned at a location where a needle 502 is fluidly coupled with the fluid distribution system.

In some embodiments of the present disclosure, the support base 510 can comprise three flow channels 554, 574, 576. The three flow channels each branch into two additional flow channels or terminal segments (e.g., terminal segment 558, 560) to provide a total of six flow paths. The flow channels 574, 576 can comprise the features discussed with reference to flow channel 554, including a shared segment having a terminal end, and terminal segments having outlet ends. The features of the flow channels 574, 576 in common with the flow channel 554 are not repeated here for clarity and brevity, but are incorporated here by reference.

Each of the six flow paths of the support base 510 have an end point or outlet end (e.g., outlet ends 568, 570) at a distal end portion of the terminal segments. Each of the outlet ends can be aligned along a straight line. In some embodiments, each of the six flow paths comprises a path length measured from the inflow aperture 552 to the outlet end of each flow channel.

Any of the flow channels 554, 574, 576, or a portion of a flow channel, such as the shared segment or terminal segment, can extend along a tortious path. Despite the tortious path of a flow channel 554, 574, 576, each flow channel 554, 574, 576 can have an approximately equal fluid path length or pathway volume between the inflow aperture 552 and the respective flow channel outlet end, as discussed above with respect to FIG. 8.

When a medicament is directed into the fluid distribution system through the inflow aperture 552, the medicament can accumulate in the shared segment 556 of the flow channels 554, 574, 576. As the volume of medicament accumulating in the flow channels 554, 574, 576 increases, some of the medicament will be directed toward the terminal segment 558, 560 of the flow channels. Resistance to flow along any of the shared segment 556 and terminal segment 558, 560, and the accumulation of medicament in the flow channels 554, 574, 576, cause the medicament to move into and evenly fill the shared segment 556 and terminal segment 558, 560. With medicament evenly distributed in the flow channels 554, 574, 576, additional medicament directed into the fluid distribution system will cause the medicament to move through the needles 502 to be ejected from all needles 502 at approximately at same time, same pressure, and/or same volume.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A needle array device comprising: a needle assembly having a needle base and a plurality of needle columns extending from the base, the needle base having upper and lower portions and a plurality of needle apertures extending through the needle base from a bottom surface of the lower portion toward a corresponding needle column, each needle column supporting a needle in fluid communication with a corresponding needle aperture; a support base having an upper portion, a Luer connector, and an entrance aperture extending through the Luer connector, the upper portion being couplable to the lower portion of the needle base to form a fluid distribution cavity therebetween, the fluid distribution cavity being in fluid communication with the entrance aperture and each of the plurality of needle apertures, the Luer connector being couplable to a syringe device for injecting a fluid from the syringe device through entrance aperture and toward the needle apertures of the needle assembly; and a fluid manifold disposed in the fluid distribution cavity and having a plurality of flow channels, the flow channels operative to direct a fluid from the syringe device to each of the needle apertures to cause the fluid to reach tips of the needles approximately simultaneously.

Clause 2. The needle array device of Clause 1, wherein the fluid manifold comprises a reservoir.

Clause 3. The needle array device of Clause 2, wherein the fluid manifold comprises at least two flow channels extending from the reservoir.

Clause 4. The needle array device of Clause 3, wherein a width of the reservoir is at least twice as large as a width of the flow channels.

Clause 5. The needle array device of any one of Clauses 3 or 4, wherein each of the flow channels has a smaller cross-sectional area than the reservoir for increasing a flow resistance through the channels.

Clause 6. The needle array device of Clause 5, wherein each of the flow channels has an approximately constant cross-sectional area.

Clause 7. The needle array device of any one of Clauses 5 or 6, wherein each of the flow channels has a decreasing cross-sectional area in a direction away from the reservoir.

Clause 8. The needle array device of any one of Clauses 3 to 6, wherein each of the flow channels has an approximately constant depth.

Clause 9. The needle array device of any one of Clauses 2 to 8, wherein the fluid manifold comprises two flow channels extending in opposing directions away from the reservoir.

Clause 10. The needle array device of Clause 9, wherein the two flow channels each branch into two additional flow channels to provide a total of four flow channels.

Clause 11. The needle array device of Clause 10, wherein the four flow channels each have an end point, distal to the reservoir, each of the endpoints being aligned along a straight line.

Clause 12. The needle array device of any one of Clauses 10 or 11, wherein the four flow channels each have an end point and a path length measured from the inflow aperture along a longitudinal axis to the end point of each channel, the path lengths of each of the channels being about equal.

Clause 13. The needle array device of any one of Clauses 2 to 12, wherein the fluid manifold comprises four flow channels extending in opposing directions away from the reservoir.

Clause 14. The needle array device of Clause 13, wherein the four flow channels extend in a cross-shaped pattern with the reservoir being disposed at a central position of the cross-shaped pattern.

Clause 15. The needle array device of any one of Clauses 13 or 14, wherein two of the four flow channels each branch into two additional flow channels to provide a total of six flow channels.

Clause 16. The needle array device of Clause 15, wherein the six flow channels each have an end point, distal to the reservoir, each of the endpoints being aligned along a straight line.

Clause 17. The needle array device of any one of Clauses 15 or 16, wherein the six flow channels each have an end point and a path length measured from the inflow aperture along a longitudinal axis to the end point of each channel, the path lengths of each of the channels being about equal.

Clause 18. The needle array device of any one of the preceding Clauses, wherein the fluid manifold extends from the upper portion of the support base into the fluid distribution cavity.

Clause 19. The needle array device of any one of the preceding Clauses, wherein the fluid manifold extends from the bottom surface of the lower portion of the needle base into the fluid distribution cavity.

Clause 20. The needle array device of any one of the preceding Clauses, wherein the flow channels each define a pathway volume based on width, depth, and length thereof, the pathway volumes of each of the flow channels being about equal.

Clause 21. The needle array device of any one of the preceding Clauses, wherein the needle apertures each define a cross-sectional dimension that is less than a cross-sectional dimension of each of the flow channels.

Clause 22. The needle array device of any one of the preceding Clauses, wherein the arrival of fluid to the tips of the needles is simultaneous when an approximately constant pressure is applied to the fluid.

Clause 23. The needle array device of any one of the preceding Clauses, wherein, upon exertion of an approximately constant pressure to the fluid, the arrival of fluid to the tips of the needles is simultaneous if fluid reaches each of the needle tips within a time period of less than 20% of the total time for fluid to first reach the needle tips.

Clause 24. The needle array device of Clause 23, wherein the arrival of fluid to the tips of the needles is simultaneous if fluid reaches each of the needle tips within a time period of less than 10% of the total time for fluid to first reach the needle tips.

Clause 25. The needle array device of Clause 23, wherein the arrival of fluid to the tips of the needles is simultaneous if fluid reaches each of the needle tips within a time period of less than 5% of the total time for fluid to first reach the needle tips.

Clause 26. The needle array device of Clause 23, wherein the arrival of fluid to the tips of the needles is simultaneous if fluid reaches each of the needle tips within a time period of less than 2% of the total time for fluid to first reach the needle tips.

Clause 27. The needle array device of any one of the preceding Clauses, wherein, upon exertion of an approximately constant pressure to the fluid, an amount of fluid expelled from each of the needles is about equal.

Clause 28. The needle array device of any one of the preceding Clauses, wherein, upon exertion of an approximately constant pressure to the fluid, an amount of fluid expelled from each of the needles is between about 5 μL and about 500 μL.

Clause 29. The needle array device of any one of the preceding Clauses, wherein, upon exertion of an approximately constant pressure to the fluid, an amount of fluid expelled from each of the needles is about equal.

Clause 30. The needle array device of any one of the preceding Clauses, wherein, upon exertion of an approximately constant pressure to the fluid, an amount of fluid expelled from any one of the needles is no greater than 30% more than an amount of fluid expelled from any other one of the needles.

Clause 31. The needle array device of any one of the preceding Clauses, wherein, upon exertion of an approximately constant pressure to the fluid, an amount of fluid expelled from any one of the needles is no greater than 20% more than an amount of fluid expelled from any other one of the needles.

Clause 32. The needle array device of any one of the preceding Clauses, wherein, upon exertion of an approximately constant pressure to the fluid, an amount of fluid expelled from any one of the needles is no greater than 10% more than an amount of fluid expelled from any other one of the needles.

Clause 33. The needle array device of any one of the preceding Clauses, further comprising a sleeve having a plurality of heads, each head defining a height, each of the needles defining a height, wherein the height of the heads is less than the height of the needles to define an exposed height of the needles, the exposed height of the needles being between about 0.5 mm and about 5 mm to permit the needles to penetration and fluid deposition within a subject to a depth about equal to the exposed height.

Clause 34. The needle array device of Clause 33, wherein the exposed height is between about 1 mm and about 5 mm.

Clause 35. The needle array device of Clause 33, wherein the exposed height is between about 2 mm and about 4 mm.

Clause 36. The needle array device of Clause 33, wherein the exposed height is about 3 mm.

Clause 37. A needle array system comprising the needle array device of any one of the preceding Clauses, further comprising a syringe device couplable to the support base.

Clause 38. The system of Clause 37, further comprising a protector couplable to the needle assembly for protecting the needles prior to and after an injection procedure.

Clause 39. A needle array device comprising: a needle base having a plurality of needle apertures extending through the needle base, and a needle in fluid communication with each needle aperture; and a fluid manifold having an inflow aperture and a plurality of flow channels in fluid communication with each needle aperture; wherein a length of a fluid path from the inflow aperture to each of the plurality of needle apertures is approximately equal.

Clause 40. The needle array device of Clause 39, wherein each of the plurality of flow channels comprises a pathway volume between the inflow aperture and a respective one of each of the plurality of needle apertures, and wherein the pathway volume of each of the plurality of flow channels is approximately equal.

Clause 41. The needle array device of any of Clauses 39 or 40, wherein each of the plurality of flow channels comprises a width that tapers between the inflow aperture and each of the plurality of needle apertures Clause 42. The needle array device of any of Clauses 39 to 41, further comprising any of the features recited in Clauses 1 to 38.

Clause 43. A needle array device comprising: a needle base having a plurality of needle apertures extending through the needle base, and a needle in fluid communication with each needle aperture; and a fluid manifold having an inflow aperture and a plurality of flow channels in fluid communication with each needle aperture; wherein each of the plurality of flow channels comprises a pathway volume between the inflow aperture and a respective one of each of the plurality of needle apertures, and wherein the pathway volume of each of the plurality of flow channels is approximately equal.

Clause 44. The needle array device of Clause 43, wherein a length of a fluid path from the inflow aperture to each of the plurality of needle apertures is approximately equal.

Clause 45. The needle array device of any of Clauses 43 or 44, wherein a volume of a reservoir in fluid communication between the inflow aperture and the plurality of flow channels is larger than the pathway volume of each of the plurality of flow channels.

Clause 46. The needle array device of any of Clauses 43 to 45, further comprising any of the features recited in Clauses 1 to 42.

Clause 47. A needle array device comprising: a needle base having a plurality of needle apertures extending through the needle base, and a needle in fluid communication with each needle aperture; and a fluid manifold having an inflow aperture and a flow channel in fluid communication with each needle aperture, the flow channel comprising a shared segment that splits in to two or more terminal segments.

Clause 48. The needle array device of Clauses 47, further comprising any of the features recited in Clauses 1 to 46.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

In one or more aspects, the terms "about," "substantially," and "approximately" may provide an industry-accepted tolerance for their corresponding terms and/or relativity between items, such as from less than one percent to ten percent.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A needle array device comprising:
   a needle assembly having a needle base and a plurality of needle columns extending from the needle base, the needle base having upper and lower portions and a plurality of needle apertures extending through the needle base from a bottom surface of the lower portion toward a corresponding needle column of the plurality of needle columns, each needle column supporting a needle in fluid communication with a corresponding needle aperture of the plurality of needle apertures;
   a support base having an upper portion, a Luer connector, and an inflow aperture in fluid communication with the Luer connector, the upper portion of the support base being couplable to the lower portion of the needle base to form a fluid distribution cavity therebetween, the fluid distribution cavity being in fluid communication with the inflow aperture and each of the plurality of needle apertures, the Luer connector being couplable to a syringe device for injecting a fluid from the syringe device through the inflow aperture and toward the needle apertures of the needle assembly; and
   a fluid manifold disposed in the fluid distribution cavity and having a plurality of flow channels, the flow channels operative to direct the fluid from the syringe device to each of the needle apertures to cause the fluid to reach tips of the needles approximately simultaneously;
   wherein when the needle assembly is coupled to the support base in an assembled configuration,
   (i) a first needle aperture of the plurality of needle apertures is spaced apart from the inflow aperture at a first distance, and a second needle aperture of the plurality of needle apertures is spaced apart from the inflow aperture at a second distance, different from the first distance,
   (ii) a first flow channel of the plurality of flow channels has a first terminal portion in fluid communication with only the first needle aperture and a second flow channel of the plurality of flow channels has a second terminal portion in fluid communication with only the second needle aperture, and
   (iii) the first flow channel defines a first pathway length from the inflow aperture to the first needle aperture and the second flow channel defines a second pathway length from the inflow aperture to the second needle aperture that is approximately equal to the first pathway length.

2. The needle array device of claim 1, wherein the fluid manifold comprises a reservoir in fluid communication with the inflow aperture.

3. The needle array device of claim 2, wherein the fluid manifold comprises at least two flow channels of the plurality of flow channels extending from the reservoir.

4. The needle array device of claim 3, wherein a width of the reservoir is at least twice as large as a width of the at least two flow channels.

5. The needle array device of claim 3, wherein each of the at least two flow channels has a smaller cross-sectional area than the reservoir for increasing a flow resistance through the at least two flow channels.

6. The needle array device of claim 5, wherein each of the at least two flow channels has an approximately constant cross-sectional area.

7. The needle array device of claim 5, wherein each of the at least two flow channels has a decreasing cross-sectional area in a direction away from the reservoir.

8. The needle array device of claim 3, wherein each of the at least two flow channels has an approximately constant depth.

9. The needle array device of claim 2, wherein the fluid manifold comprises two flow channels of the plurality of flow channels extending in opposing directions away from the reservoir.

10. The needle array device of claim 9, wherein the two flow channels each branch into two additional flow channels to provide a total of four flow channels.

11. The needle array device of claim 2, wherein the fluid manifold comprises four flow channels of the plurality of flow channels extending in opposing directions away from the reservoir.

12. The needle array device of claim 11, wherein the four flow channels extend in a cross-shaped pattern with the reservoir being disposed at a central position of the cross-shaped pattern.

13. The needle array device of claim 1, wherein the flow channels each define a pathway volume based on width, depth, and length thereof, the pathway volumes of each of the flow channels being about equal.

14. A needle array system comprising the needle array device of claim 1, and further comprising the syringe device couplable to the support base.

15. A needle array device comprising:
a needle base having a plurality of needle apertures extending through the needle base, and a plurality of needles, each needle in fluid communication with a respective needle aperture of the plurality of needle apertures; and
a fluid manifold having an inflow aperture and a plurality of flow channels in fluid communication with each needle aperture;
wherein select ones of the plurality of needle apertures are each spaced apart from the inflow aperture at different distances and each lie alone in a terminal portion of one of the plurality of flow channels, and wherein fluid pathways from the inflow aperture to the select ones of the plurality of needle apertures are approximately equal to each other.

16. The needle array device of claim 15, wherein each of the plurality of flow channels comprises a pathway volume between the inflow aperture and a respective one of the plurality of needle apertures, and wherein the pathway volume of each of the plurality of flow channels is approximately equal.

17. The needle array device of claim 15, wherein each of the plurality of flow channels comprises a width that tapers between the inflow aperture and each of the plurality of needle apertures.

18. A needle array device comprising:
a needle base having first and second needle apertures extending through the needle base and a plurality of needles each in respective fluid communication with the first and second needle apertures; and
a fluid manifold having an inflow aperture and first and second flow channels each having a terminal portion, the terminal portions being in respective fluid communication with only the first or second needle apertures;
wherein (i) the first and second needle apertures are spaced at different distances from the inflow aperture and (ii) the first and second flow channels a define approximately equal pathway lengths measured from the inflow aperture the first or second needle apertures.

19. The needle array device of claim 18, wherein a volume of a reservoir in fluid communication between the inflow aperture and the first and second flow channels is larger than a pathway volume of each of the first and second flow channels.

20. The needle array device of claim 18, wherein a pathway volume of the first flow channel is approximately equal to a pathway volume of the second flow channel.

* * * * *